United States Patent [19]

Narula et al.

[11] Patent Number: 5,081,262

[45] Date of Patent: Jan. 14, 1992

[54] SUBSTITUTED CYCLOPENTENYL OXABICYCLOOCTANES, CYCLOPENTENYLFORMYLCYCLOHEXENES AND CYCLOPENTENYLHYDROXYMETHYL CYCLOHEXENES, PROCESSES FOR PREPARING SAME AND ORGANOLEPTIC USES THEREOF

[75] Inventors: Anubhav P. S. Narula, Hazlet; John J. De Virgilio, Freehold, both of N.J.; Carlos Benaim, Bedford Hills, N.Y.; Anton Van Ouwerkerk, Livingston, N.J.; Olivier Gillotin, Denville, N.J.

[73] Assignee: International Flavors & Fragrances Inc., New York, N.Y.

[21] Appl. No.: 588,825

[22] Filed: Sep. 27, 1990

[51] Int. Cl.[5] .............................. C07C 313/06
[52] U.S. Cl. ................................ 549/355; 549/398; 568/446; 568/816
[58] Field of Search ............... 549/355, 398; 568/446, 568/816

[56] References Cited

U.S. PATENT DOCUMENTS 4,224,176  9/1980  Sprecker et al. ................... 512/13
4,267,067  5/1981  Sprecker et al. .............. 252/174.11
4,269,862  5/1981  Specker et al. ................... 426/536

OTHER PUBLICATIONS

"Perfume and Flavor Chemicals" (Aroma Chemicals) 1969 (Published by the author) Monograph 616.

*Primary Examiner*—James H. Reamer
*Attorney, Agent, or Firm*—Arthur L. Liberman

[57] ABSTRACT

Described are cyclopentenyl-oxabicyclooctanes, cyclopentenyl-formylcyclohexenes and cyclopentyl-hydroxymethyl cyclohexenes having the generic structures:

and wherein $R_1$, $R_2$, $R_3'$, and $R_3''$ each represents hydrogen or methyl with the provisos:
  (i) one or two of $R_1$, $R_2$, $R_3'$ and $R_3''$ represents methyl;
  (ii) $R_1$ and/or $R_2$ are methyl;
  (iii) at least one of $R_3'$ and $R_3''$ is hydrogen; and
  (iv) when $R_1$ and $R_2$ is methyl then each of $R_3'$ and $R_3''$ is hydrogen wherein $R_4'$ is hydrogen or $C_1$–$C_5$ alkyl, processes for preparing same and uses thereof in augmenting or enhancing the aroma of perfume compositions, colognes and perfumed articles, e.g., solid or liquid, anionic, cationic, nonionic or zwitterionic detergents, cosmetic preparations, fabric softener compositions, fabric softener articles, hair preparations and perfumed polymers.

8 Claims, 13 Drawing Sheets

GLC PROFILE FOR EXAMPLE I.

GLC PROFILE FOR EXAMPLE II.

GLC PROFILE FOR EXAMPLE III.

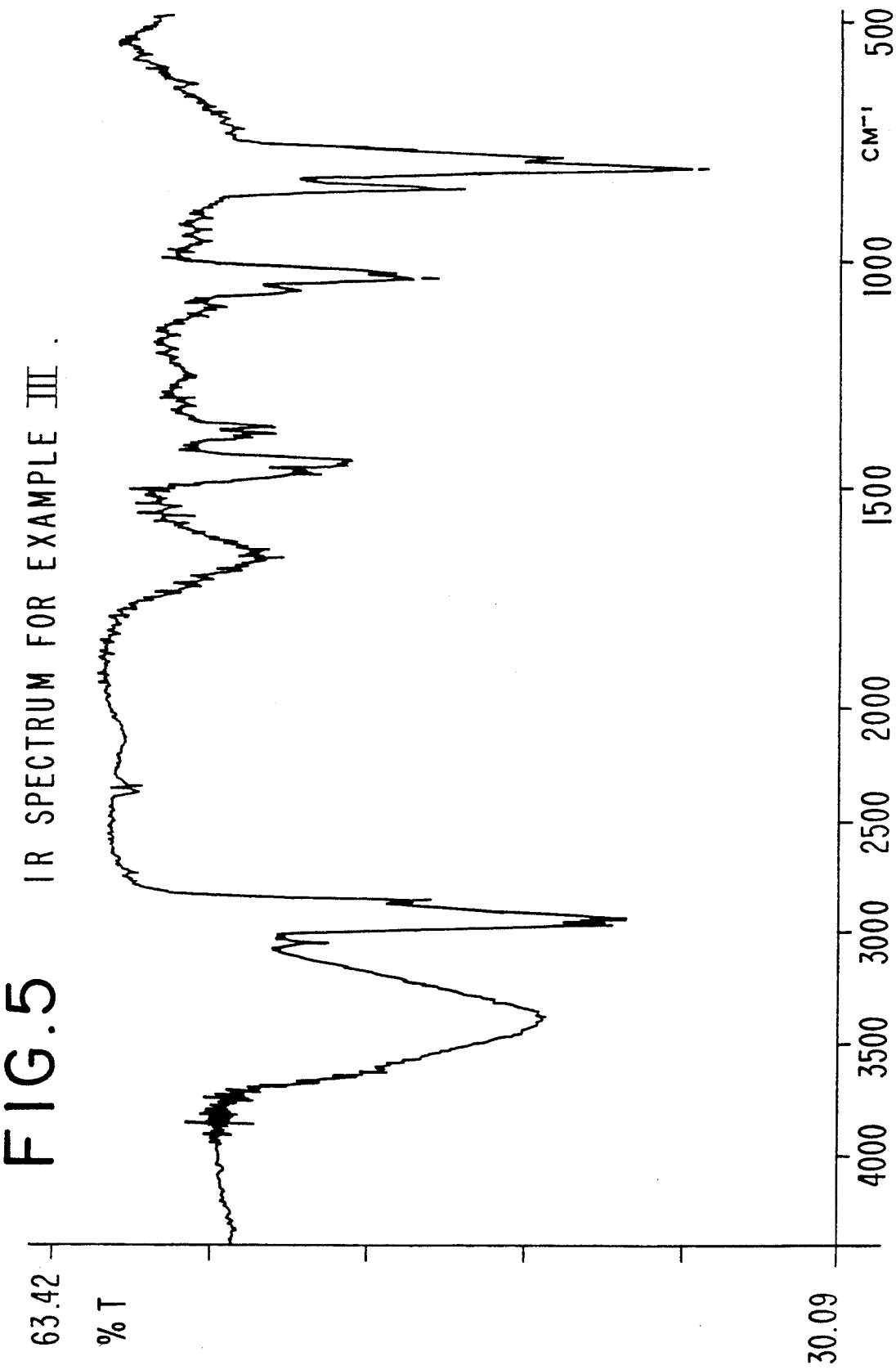
FIG. 5  IR SPECTRUM FOR EXAMPLE III.

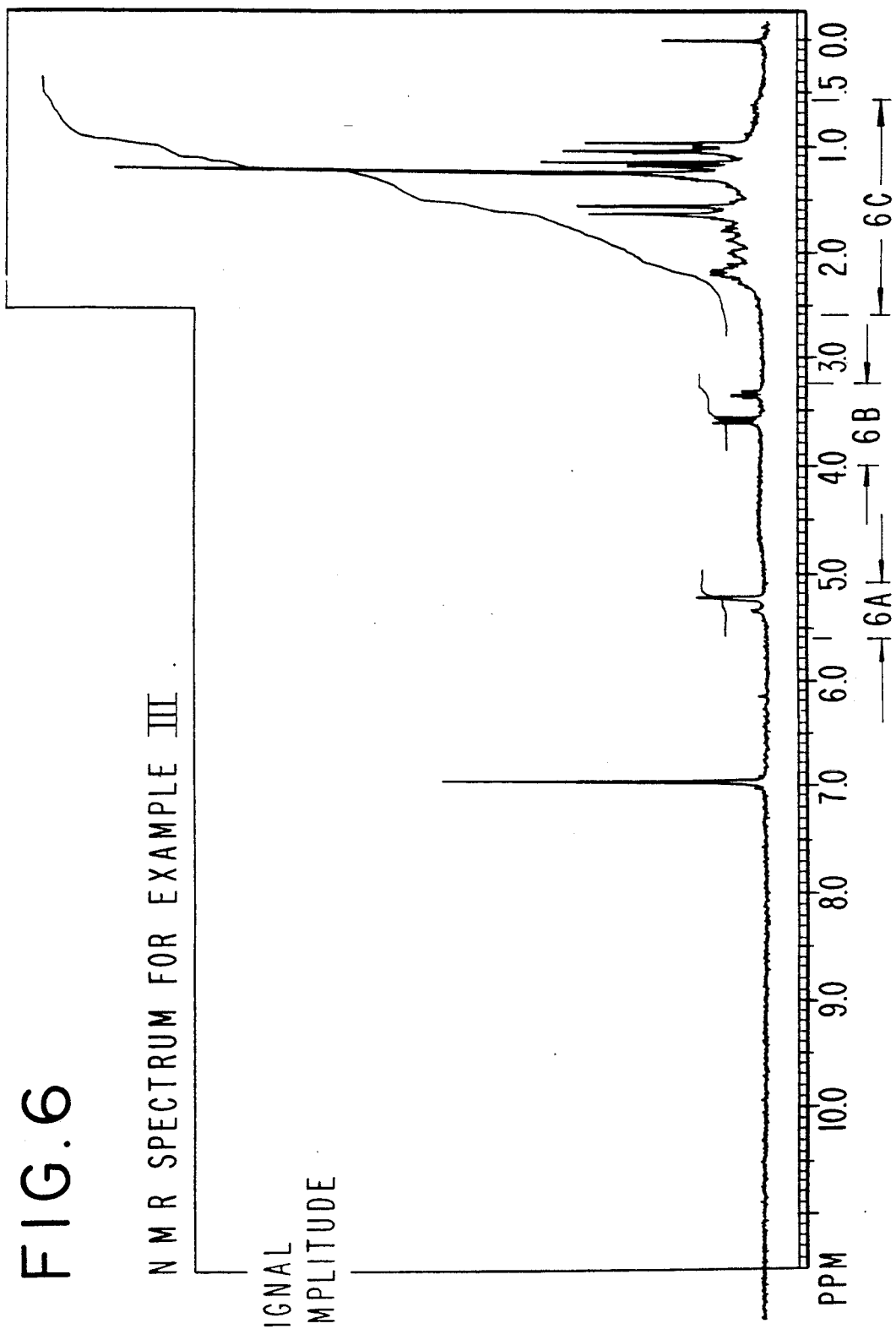
FIG. 6 NMR SPECTRUM FOR EXAMPLE III 5.4 5.2
PPM 3.6 3.4
PPM

GLC PROFILE FOR EXAMPLE IV.

FIG. 8 IR SPECTRUM FOR EXAMPLE IV.

GLC PROFILE FOR EXAMPLE V.

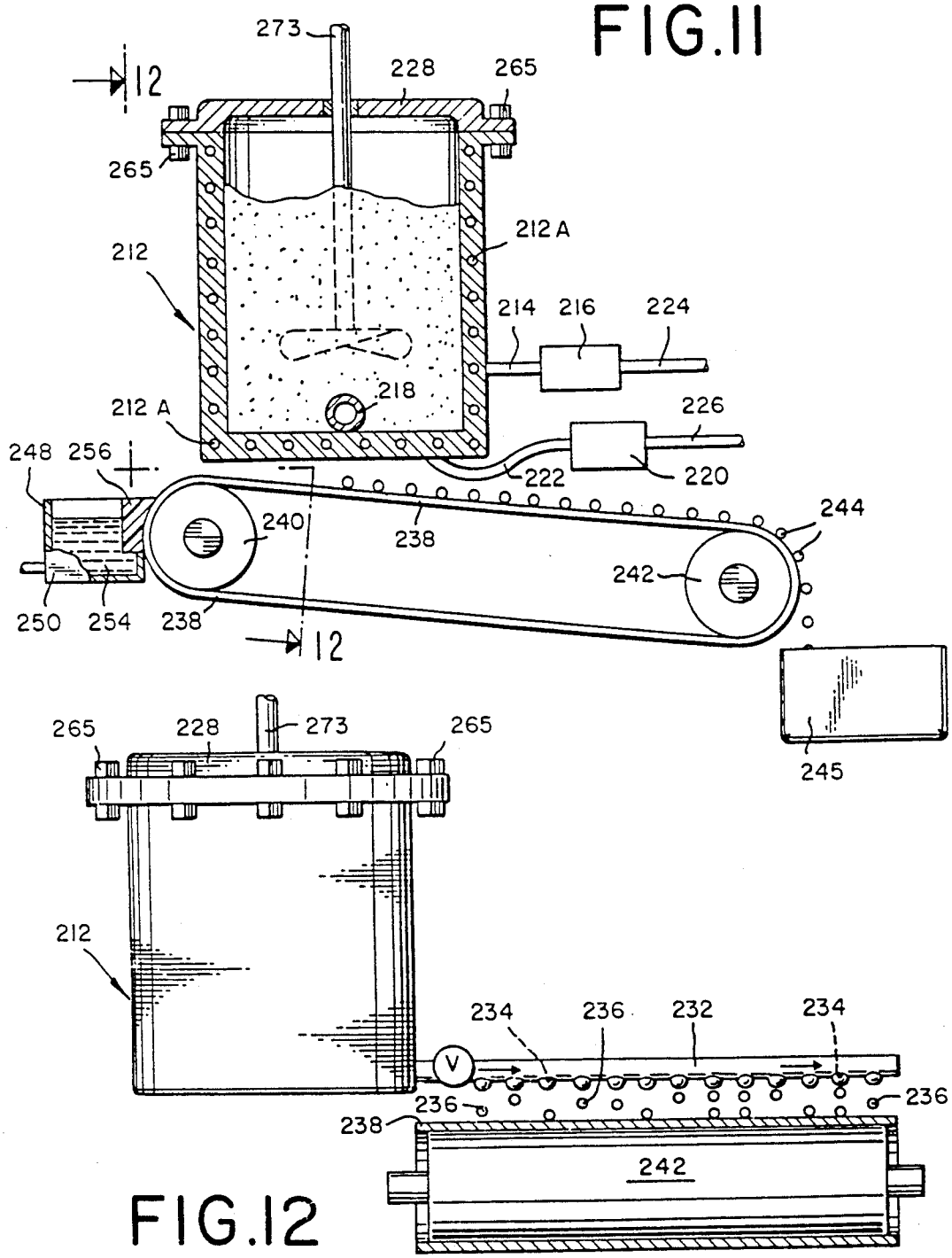

5,081,262

SUBSTITUTED CYCLOPENTENYL OXABICYCLOOCTANES, CYCLOPENTENYLFORMYLCYCLOHEXENES AND CYCLOPENTENYLHYDROXYMETHYL CYCLOHEXENES, PROCESSES FOR PREPARING SAME AND ORGANOLEPTIC USES THEREOF

BACKGROUND OF THE INVENTION

This invention relates to cyclopentenyl-oxabicyclooctanes, cyclopentenyl-formylcyclohexenes and cyclopentenyl-hydroxymethyl cyclohexenes and uses thereof in augmenting or enhancing the aroma of perfume compositions, perfumed articles and colognes.

Cassis, camphoraceous, sweaty, borneol, woody, piney, green and ozoney aromas with parsley, basil, cassis, sweaty, borneol, camphoraceous, eucalyptus bud-like, hemlock and piney topnotes are particularly desirable in augmenting or enhancing the aroma of perfume compositions, colognes and perfumed articles (e.g. solid or liquid anionic, cationic, nonionic or zwitterionic detergents, fabric softener compositions, fabric softener articles, hair preparations, cosmetic powders and perfumed polymers.

Compounds having the oxabicyclooctane nucleus have been known for use in augmenting or enhancing the aroma of perfume compositions, perfumed articles and colognes for a number of years. Thus, the compound having the structure:

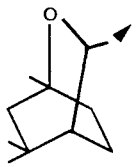

is disclosed at column 4, lines 35-40 of U.S. Letters Pat. No. 4,269,862 (Sprecker, et al. II) to have a minty, camphor, woody and piney aroma profile. U.S. Letters Pat. No. 4,269,862 further discloses the genus defined according to the structure:

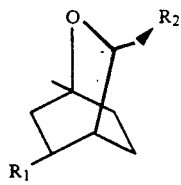

wherein $R_1$ is hydrogen or methyl and $R_2$ is $C_3$–$C_5$ alkyl or alkenyl to have utility in augmenting or enhancing the aroma of perfume compositions, colognes and perfumed articles.

Furthermore, cineole itself having the structure:

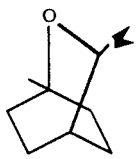

is disclosed by Arctander "Perfume and Flavor Chemicals" (Aroma Chemicals) at monograph 616 to have an eucalyptus aroma (its common name is "eucalyptol").

Nothing in the prior art, however, discloses the cyclopentenyl-oxabicyclooctanes, cyclopentenyl-formylcyclohexenes and cyclopentenyl-hydroxymethyl cyclohexenes of our invention or their organoleptic uses.

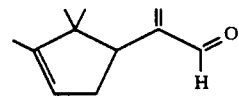

(Conditions: Carbowax column programmed at 220° C. isothermal).

Figure 2:
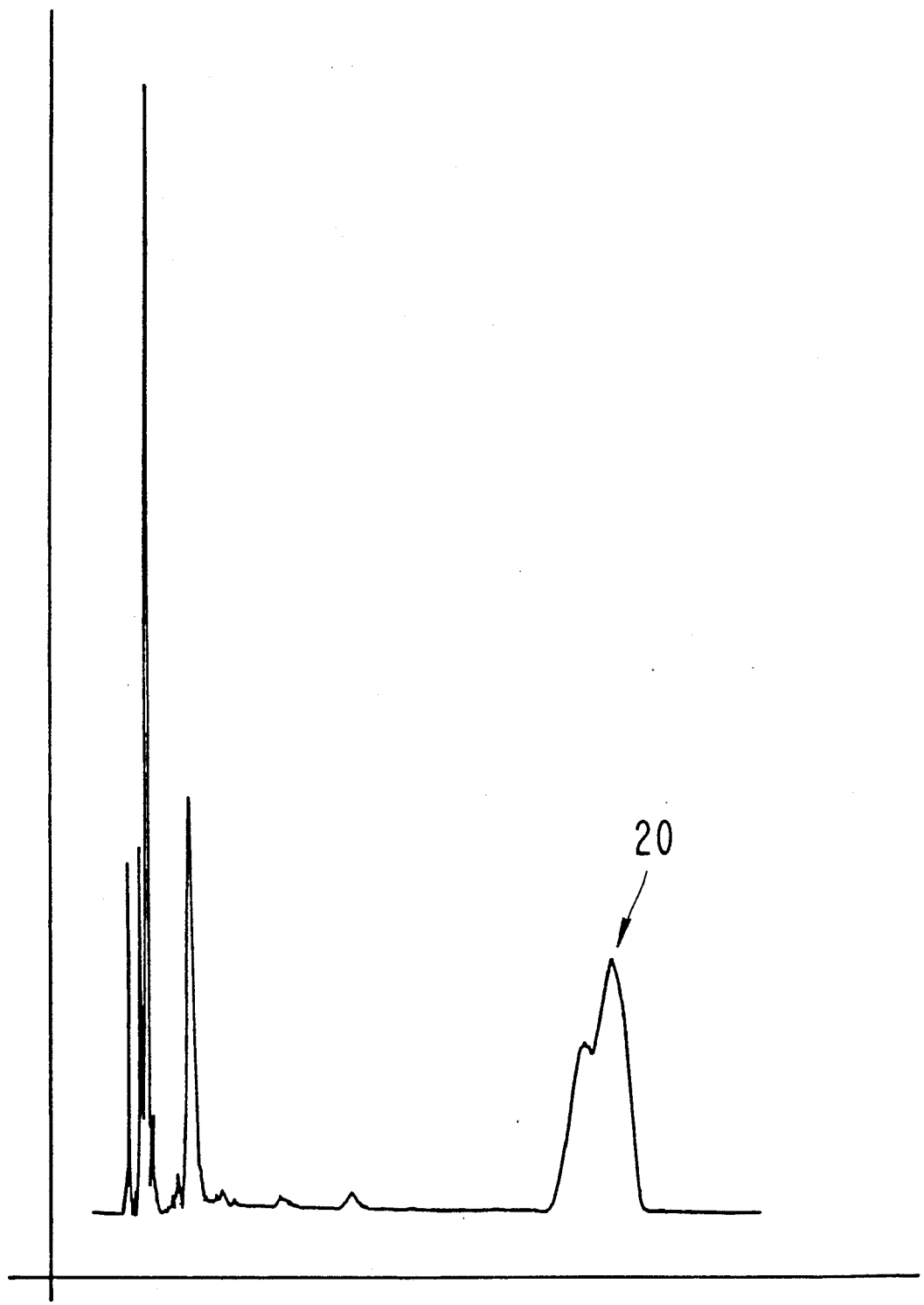

FIG. 2 is the GLC profile for the reaction product of Example II containing the mixture of compounds having the structures:

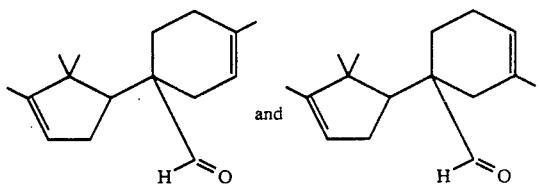

(Conditions: Carbowax column programmed at 220° C. isothermal).

Figure 3:
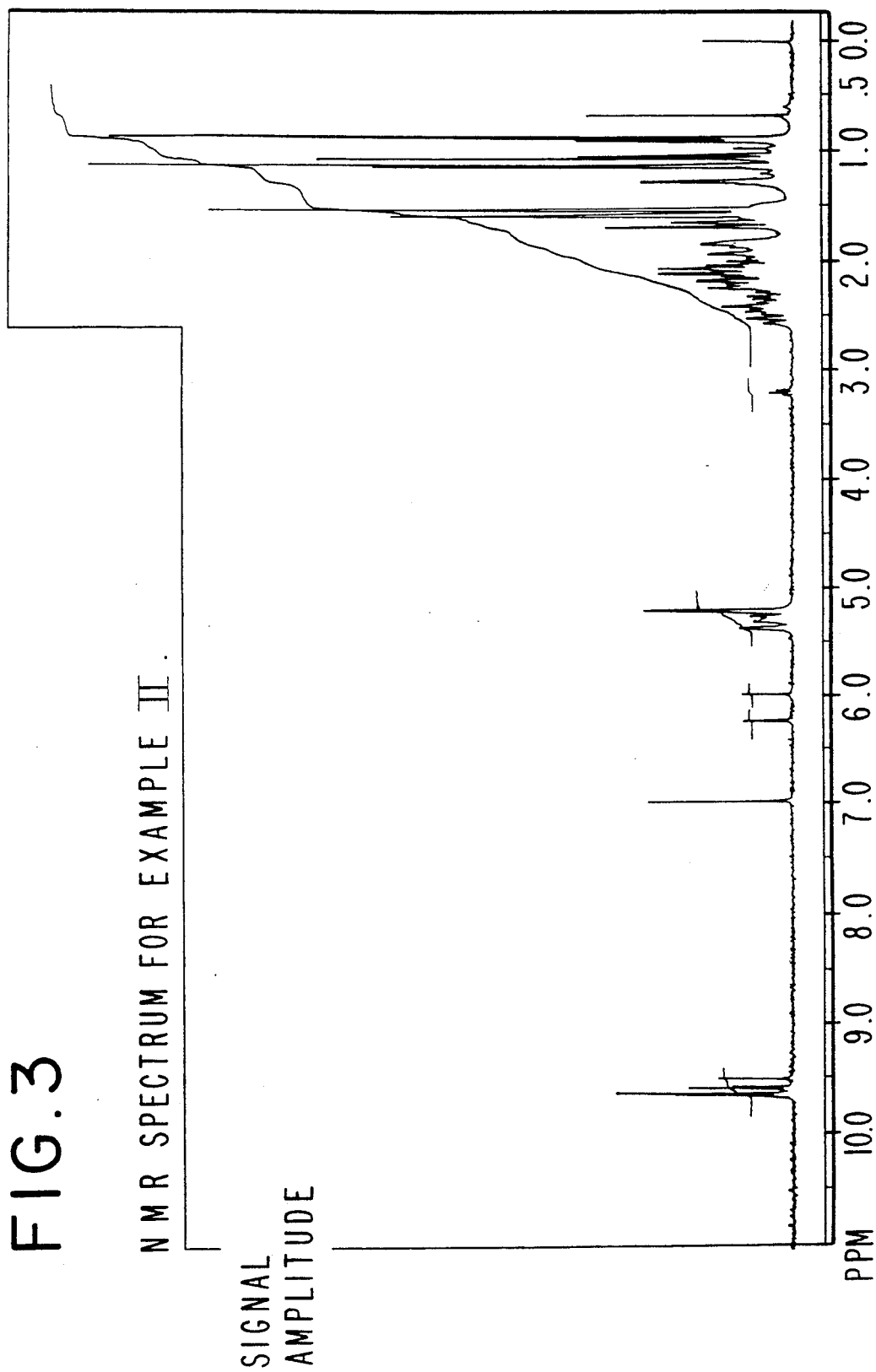

FIG. 3 is the NMR spectrum for the mixture of compounds having the structures:

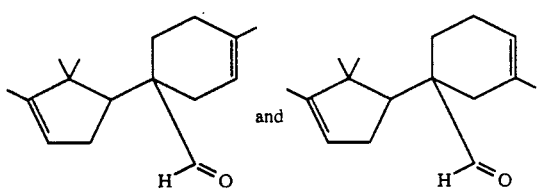

prepared according to Example II.

Figure 4:
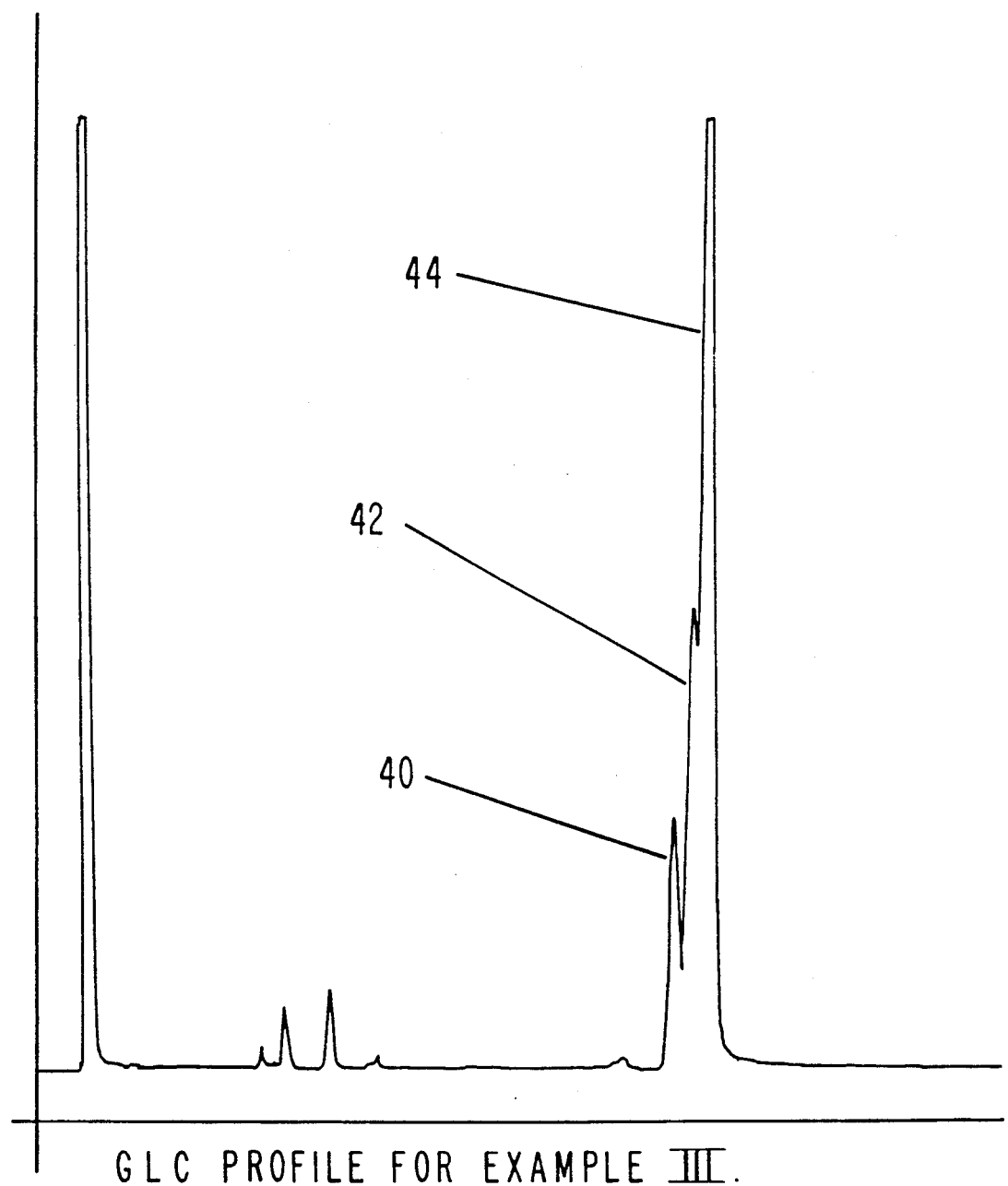

FIG. 4 is the GLC profile for the reaction product of Example III containing the compounds having the structures:

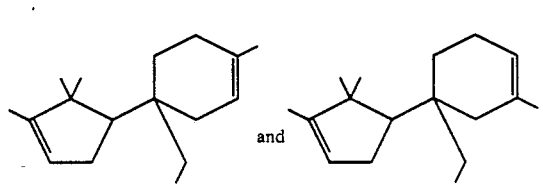

FIG. 5 is the infra-red spectrum for the mixture of compounds of Example III having the structures:

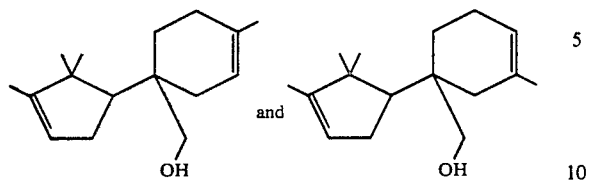

Figure 6A:
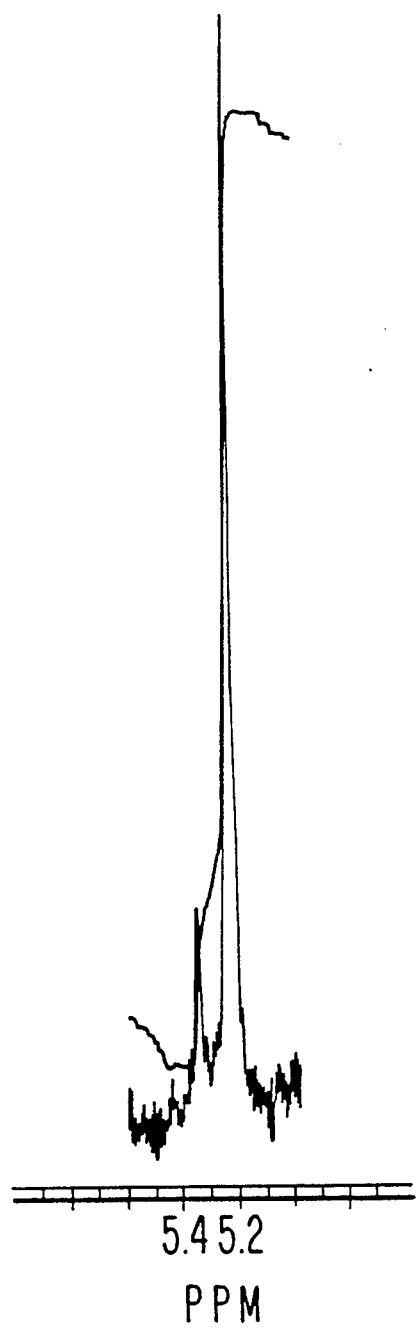
Figure 6B:
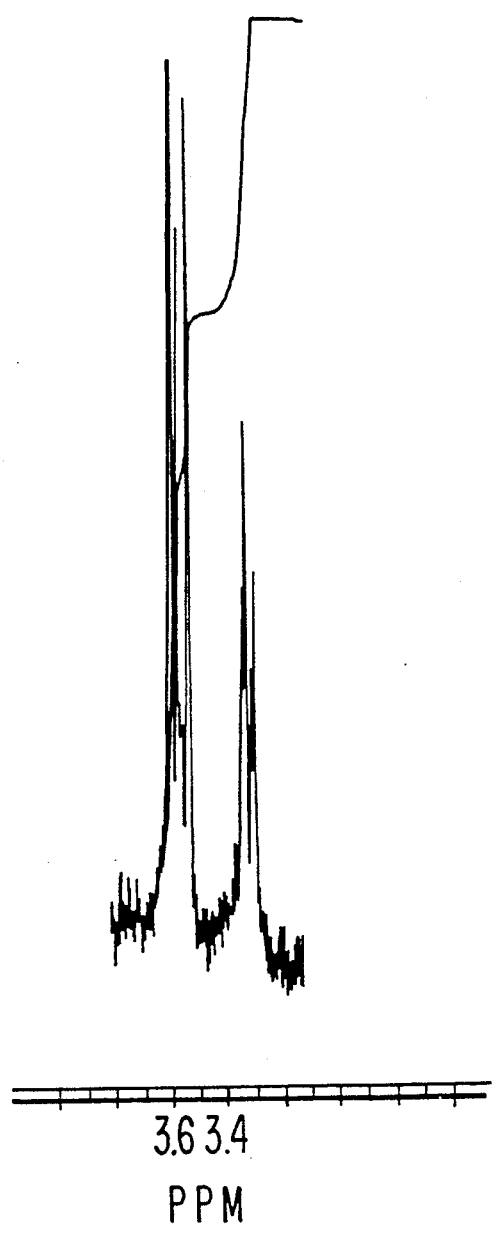
Figure 6C:
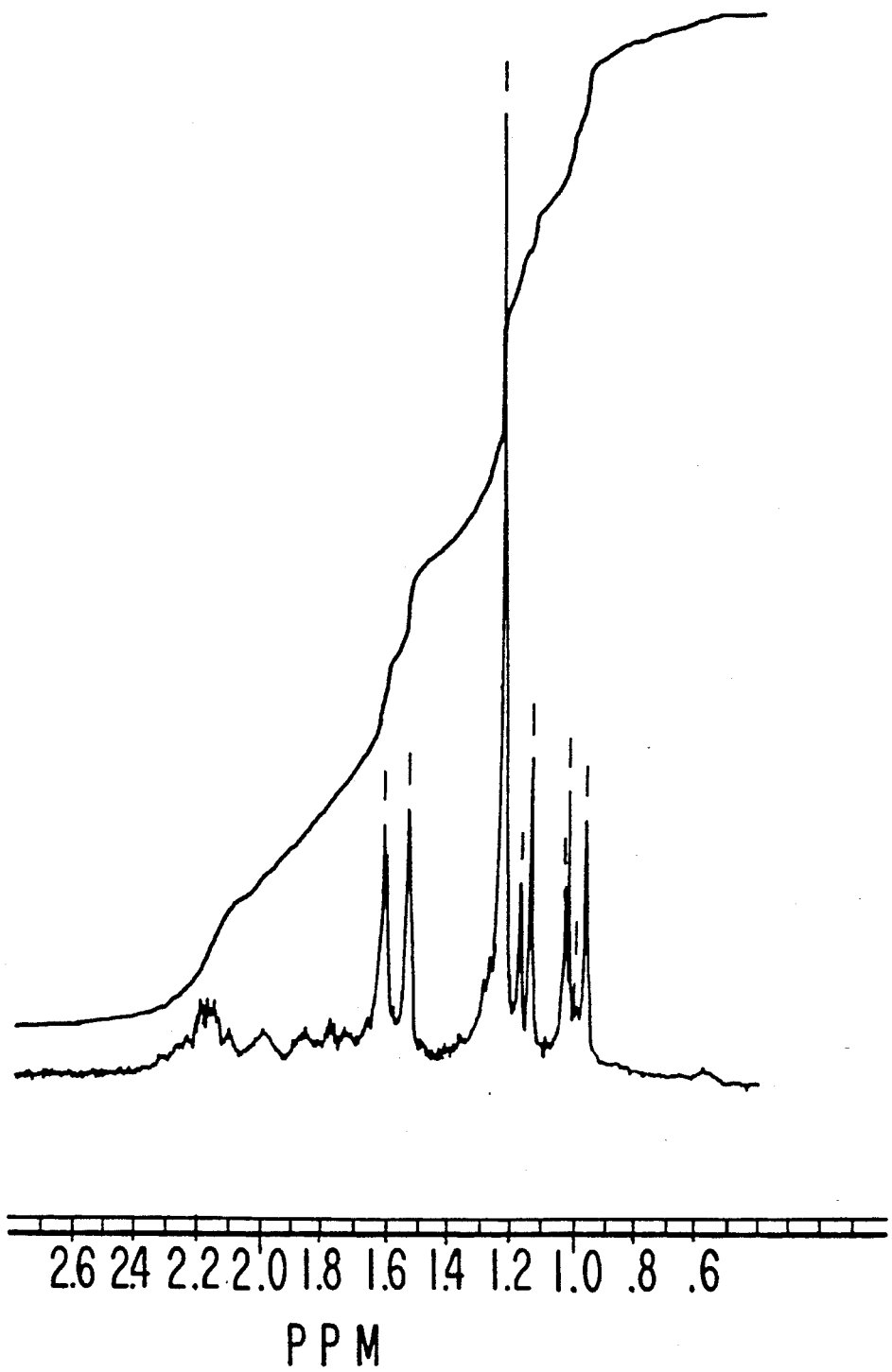

FIG. 6 is the NMR spectrum for the mixture of compounds having the structures:

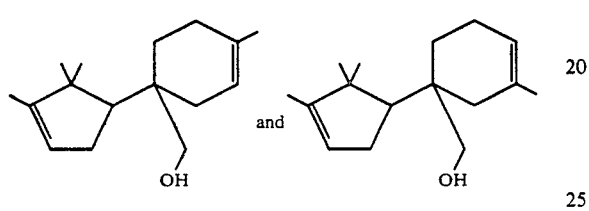

prepared according Example III.

FIGS. 6-A, 6-B and 6-C are detailed sections of the NMR spectrum of FIG. 6.

Figure 7:
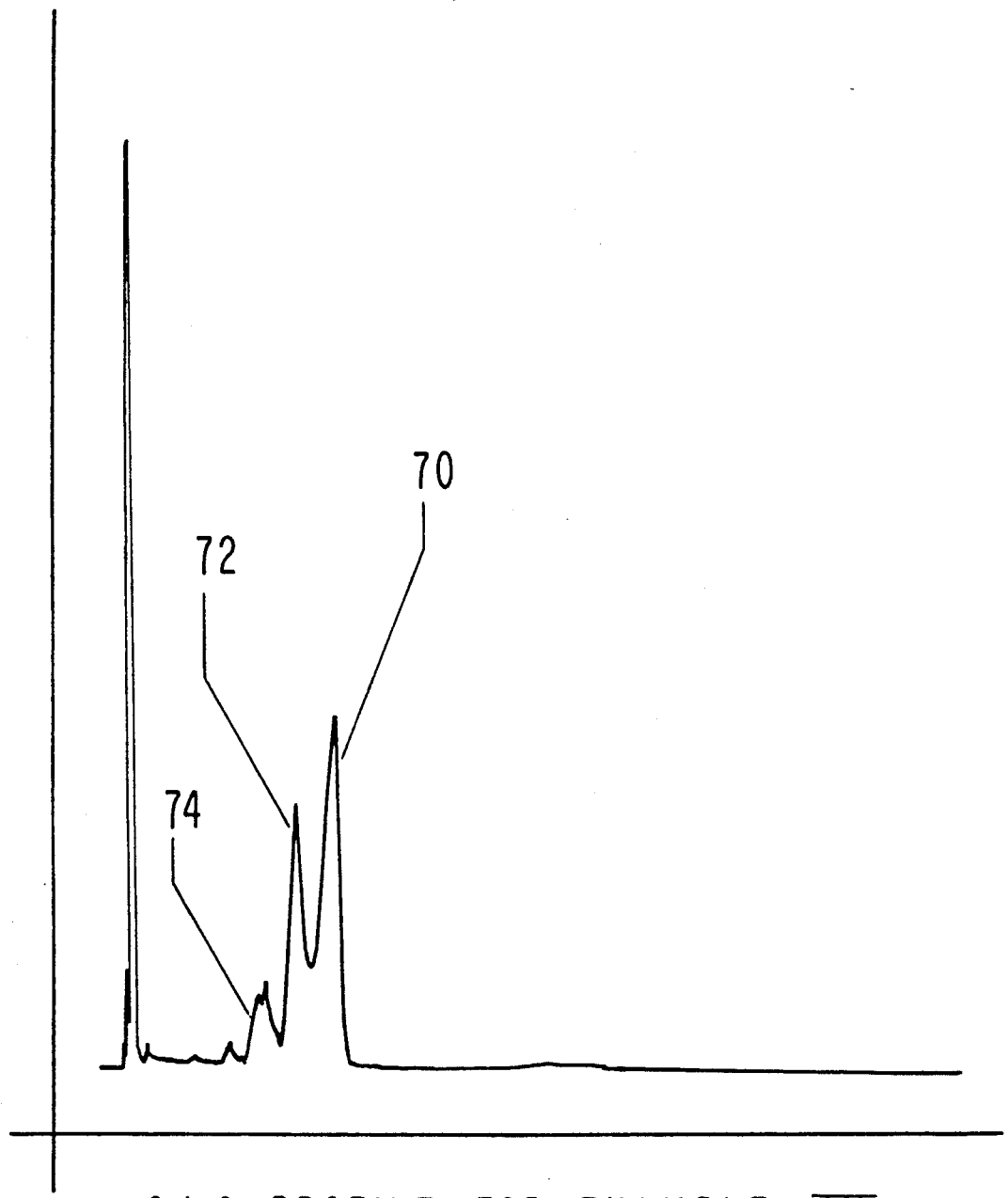

FIG. 7 is the GLC profile for the reaction product of Example IV containing the compounds having the structures:

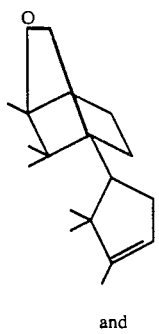

and

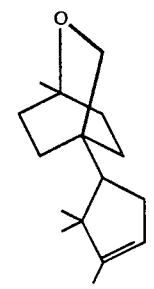

Figure 8:
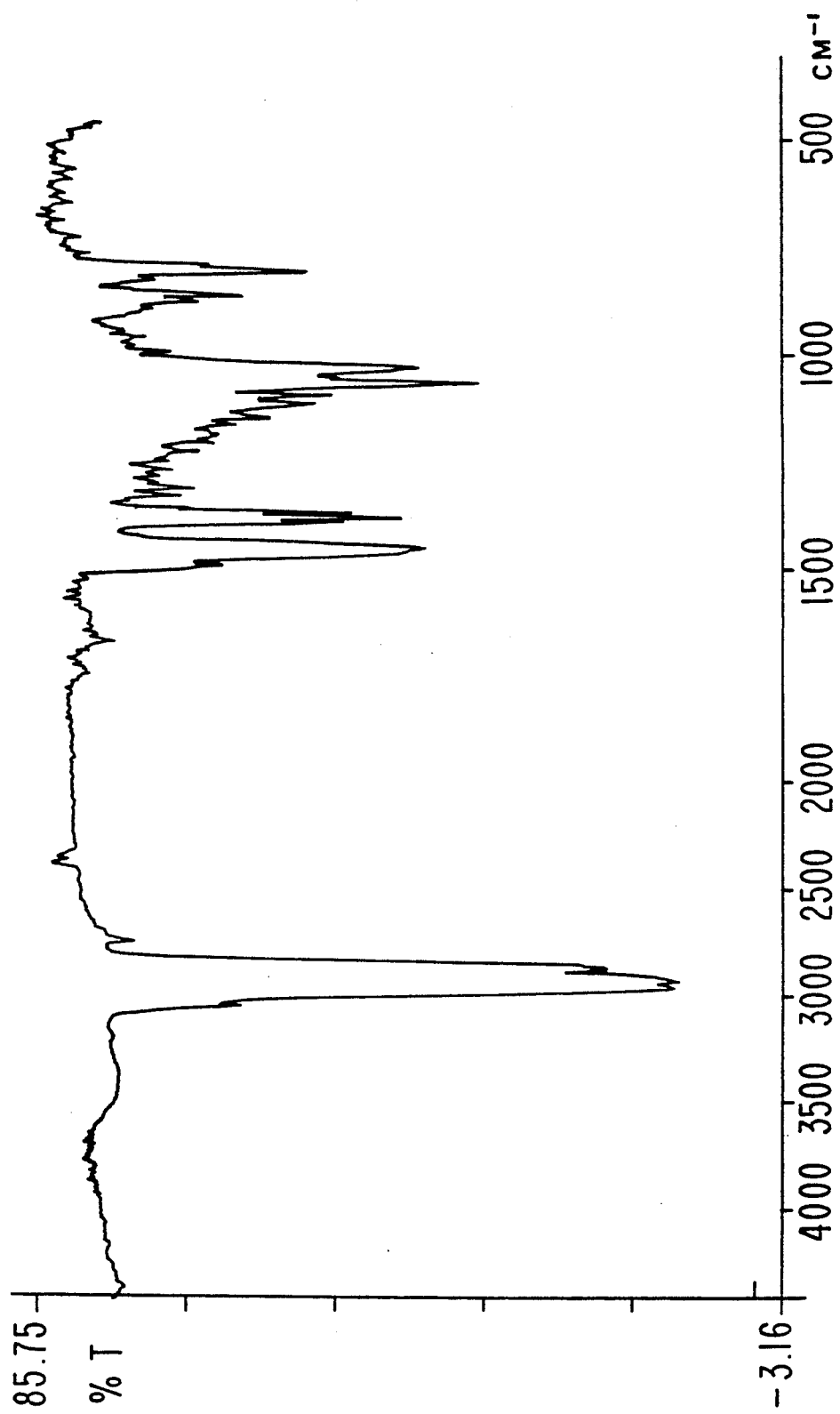

FIG. 8 is the infra-red spectrum for the mixture of compounds having the structures:

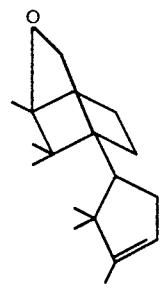

and

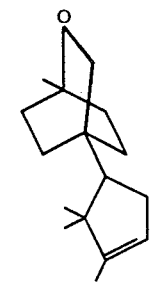

prepared according to according to Example IV.

Figure 9:
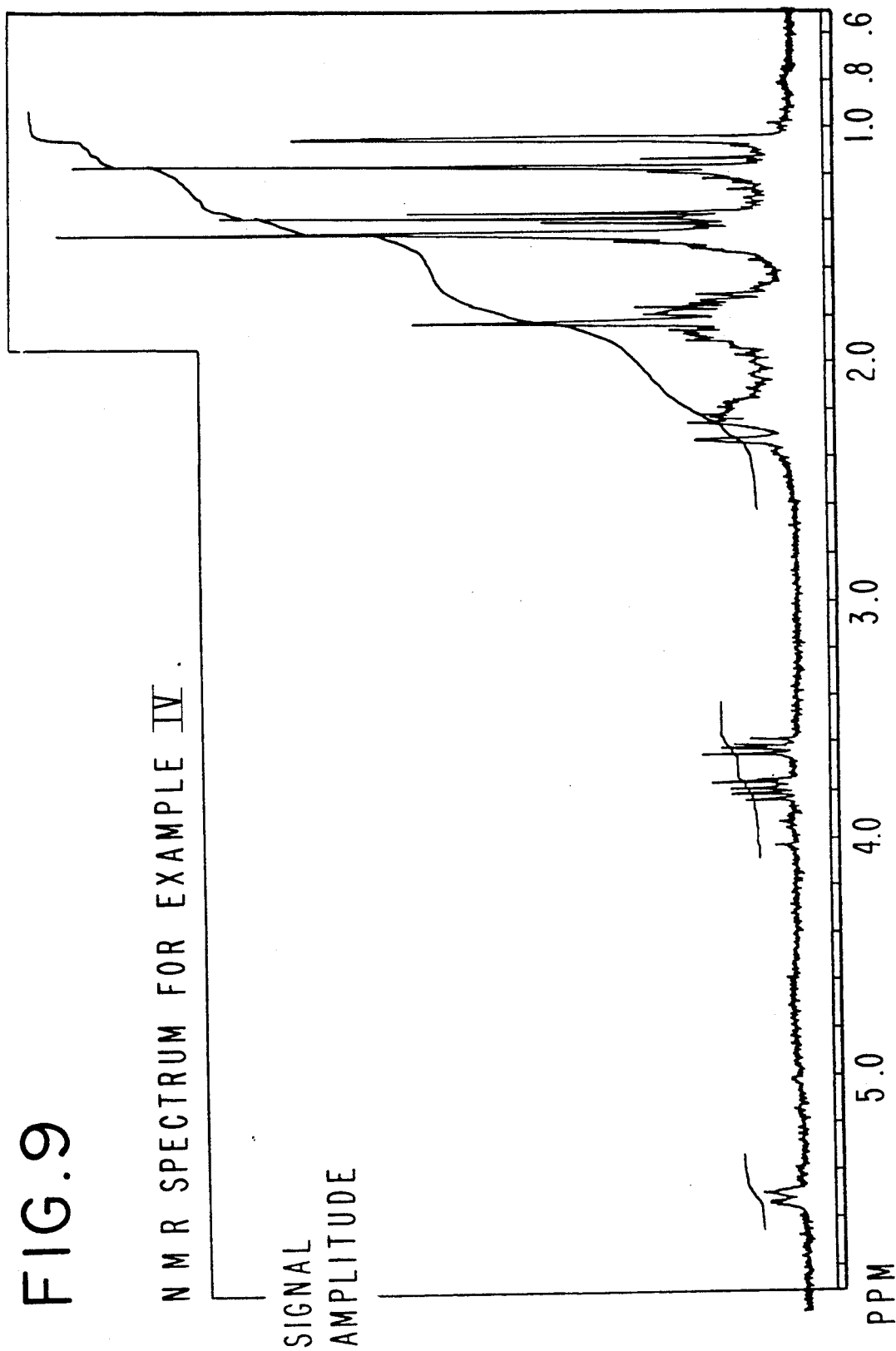

FIG. 9 is the NMR spectrum for the mixture of compounds having the structures:

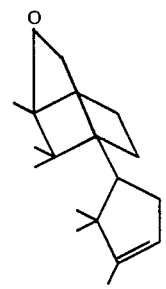

and

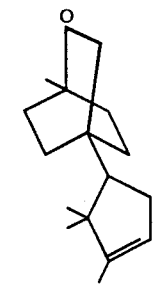

prepared according to Example IV.

Figure 10:
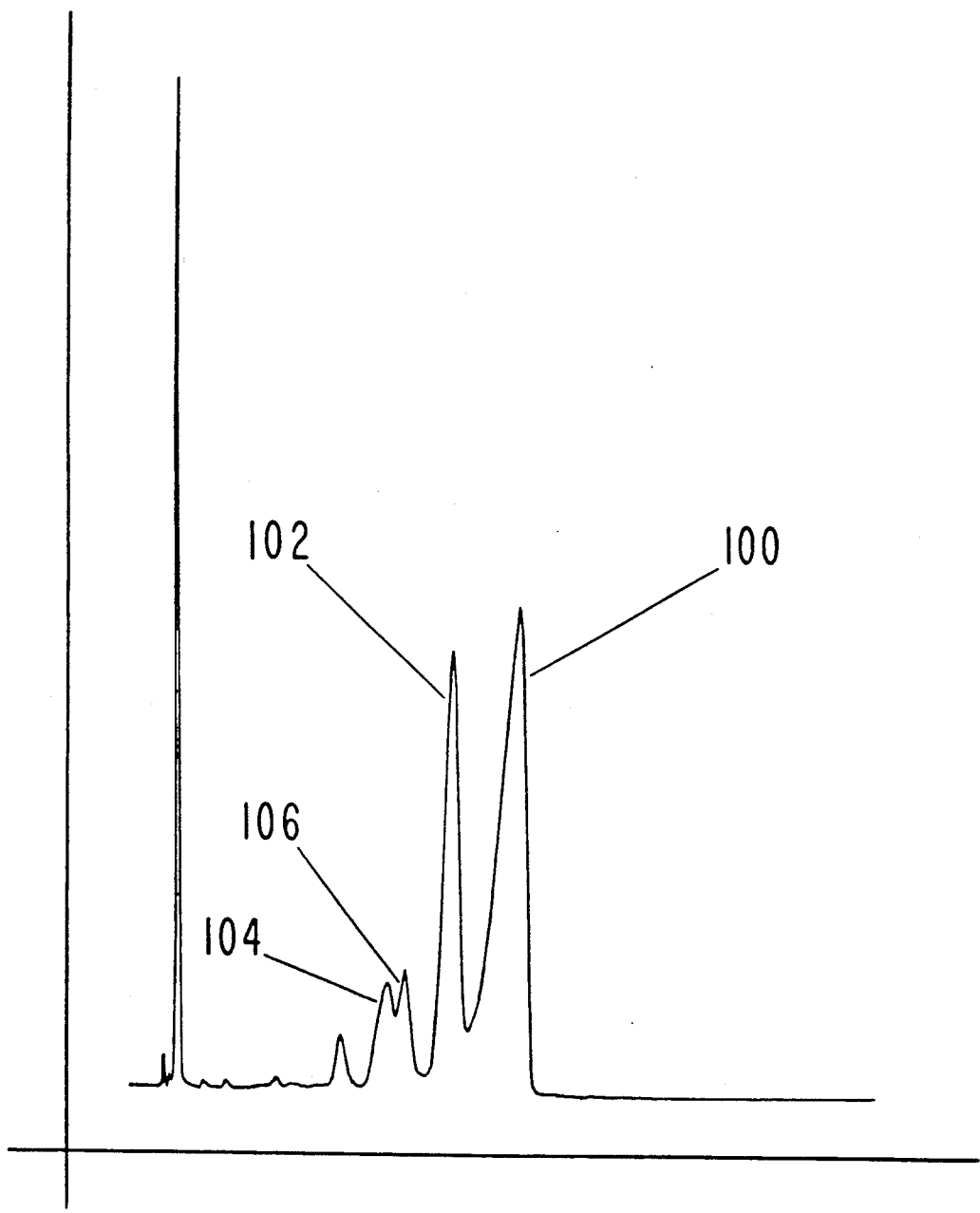

FIG. 10 is the GLC profile for the reaction product of Example V containing the compounds having the structures:

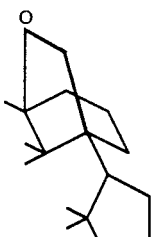

and

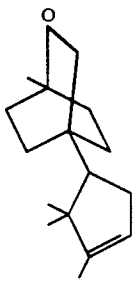

(Conditions: Carbowax column programmed at 220° C. isothermal).

FIG. 11 is a partial side elevation and partial sectional view of an apparatus for forming polymer pellets scented with one of the perfume compositions or perfumery materials of our invention containing at least one of the cyclopentenyl-oxabicyclooctanes, cyclopentenyl-formylcyclohexenes and cyclopentenyl-hydroxymethyl cyclohexenes of our invention.

FIG. 12 is section taken on line 12—12 of FIG. 11.

DETAILED DESCRIPTION OF THE DRAWINGS

Figure 1:
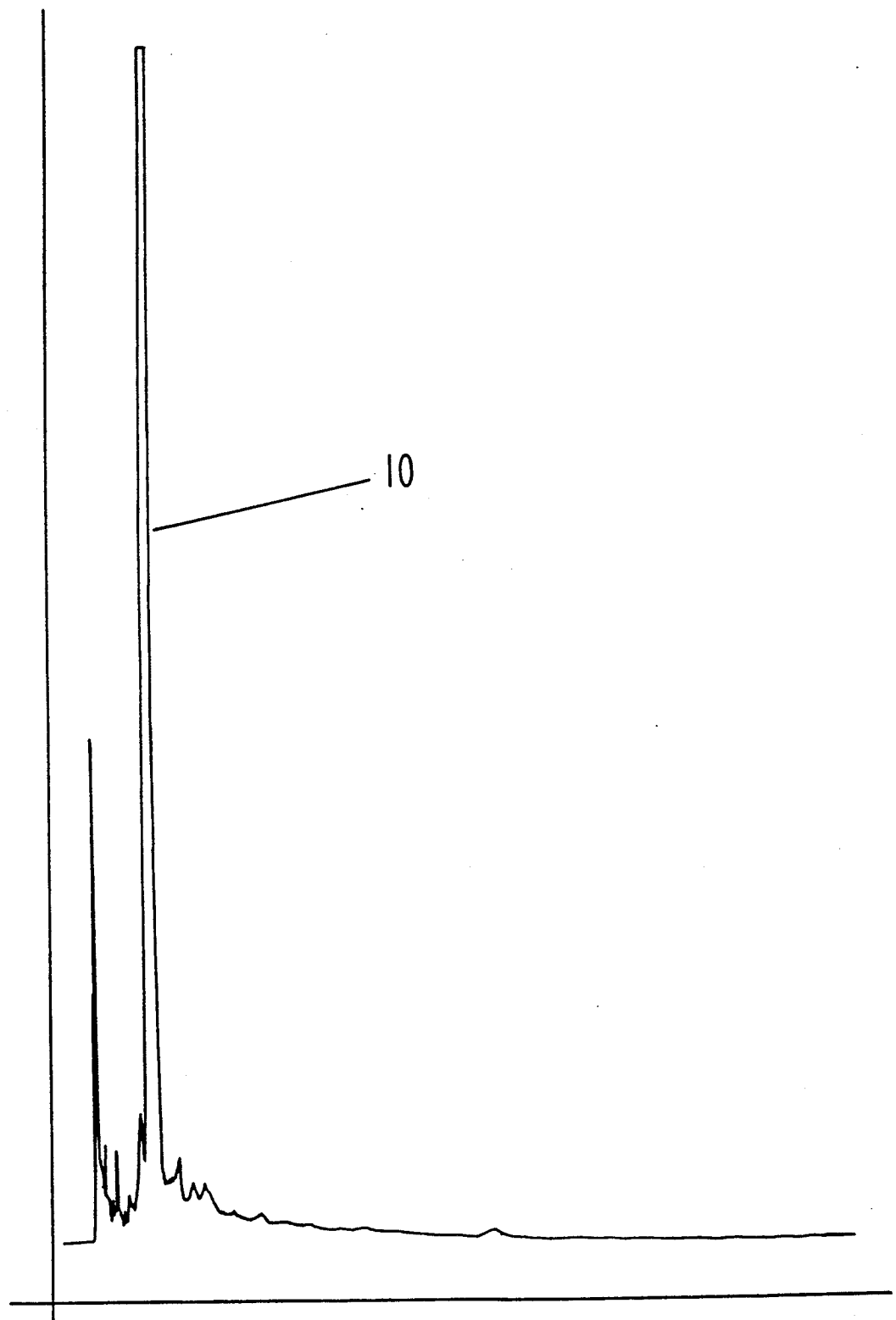
FIG. 1 is the GLC profile for the reaction product of Example I containing the compound having the structure.

FIG. 1 is the GLC profile for the reaction product of Example I containing the compound having the structure:

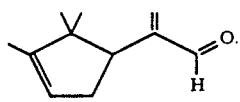

The peak indicated by reference numeral 10 is the peak for the compound having the structure:

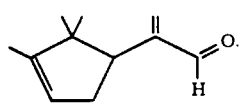

(Conditions: Carbowax column programmed at 220° C. isothermal).

FIG. 2 is the GLC profile for the reaction product of Example II containing the compounds having the structures:

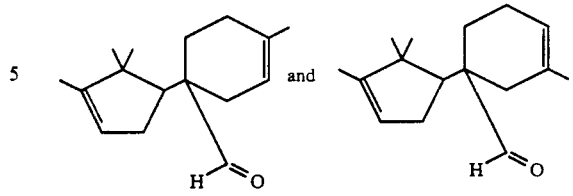

The group of peaks indicated by reference numeral 20 are peaks for isomers of the compounds having the structures:

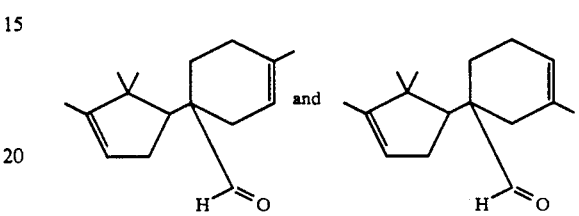

FIG. 4 is the GLC profile for the reaction product of Example III containing the compounds having the structures:

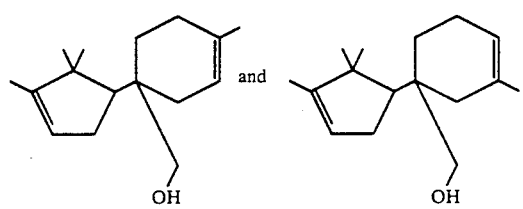

(Conditions: Carbowax column programmed at 150°-220° C.).

The peaks indicated by reference numerals 40, 42 and 44 are peaks for isomers of the compounds having the structures:

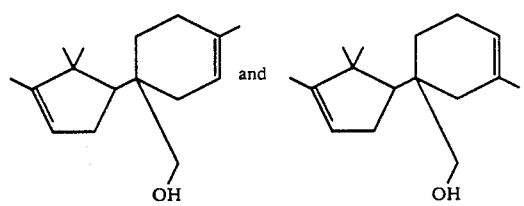

FIG. 6 is the NMR spectrum for the mixture of compounds having the structures:

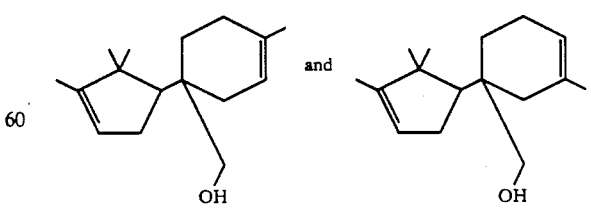

prepared according to Example III. Sections of the NMR spectrum indicated by the references 6-A, 6-B and 6-C, respectively, are set forth in detail in FIGS. 6-A, 6-B and 6-C.

FIG. 7 is the GLC profile for the reaction product of Example IV containing the compounds having the structures:

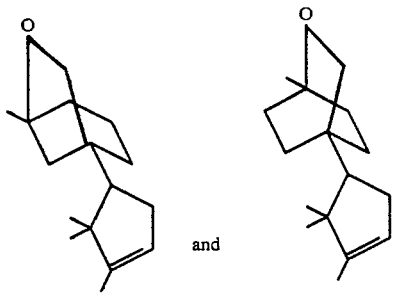

and (Conditions: Carbowax column programmed at 220° C. isothermal).

The peaks indicated by reference numerals 70, 72 and 74 are peaks for isomers of the compounds having the structures:

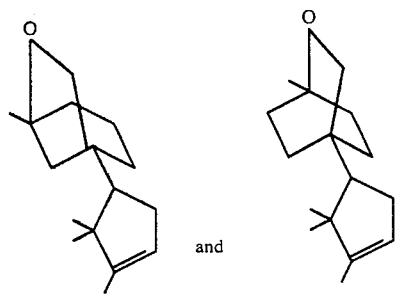

and

FIG. 10 is the GLC profile for the reaction product of Example V containing the compounds having the structures:

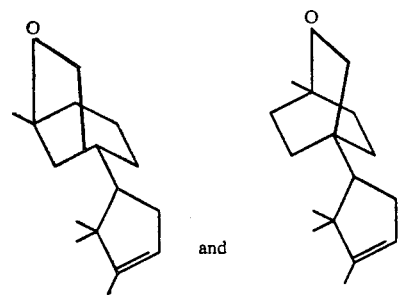

and (Conditions: Carbowax column programmed at 200° C. isothermal).

The peaks indicated by reference numerals 100, 102, 104 and 106 are peaks for isomers of the compounds having the structures:

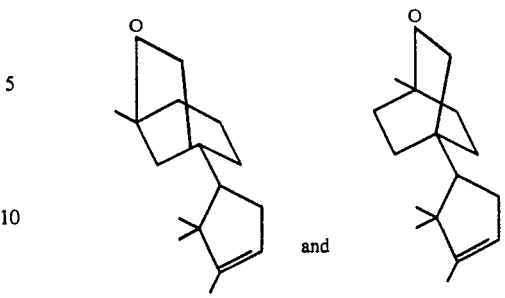

and

Referring to FIGS. 11 and 12, the apparatus used in producing polymeric fragrances containing at least one of the cyclopentenyl-oxabicyclooctanes, cyclopentenyl-formylcyclohexenes and cyclopentenyl-hydroxymethyl cyclohexenes of our invention comprises a device for forming scented polyolefin (for example) pellets which comprises a vat or container 212 into which a mixture of polyolefins such as polyethylene or an aromatic substance or scented material containing or consisting of at least one of the cyclopentenyl-oxabicyclooctanes, cyclopentenyl-formylcyclohexenes and cyclopentenyl-hydroxymethyl cyclohexenes of our invention is placed. The container is closed by an air tight lid 228 and clamped to the container by bolts 265. A stirrer 273 traverses the lid or cover 228 in air tight manner and is rotated in a suitable manner. A surrounding cylinder 212 having heating coils which are supplied with electric current through cable 224 from a rheostat or control 216 is operated to maintain the temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200°-280° F. The heater 212-A is operated to maintain the upper portion of the container 212 within a temperature range of from 250°-350° F. The bottom portion of the container 212 is heated by means of heating coils 212-A heated through a control 220 connected thereto through a connecting wire 226 to maintain the lower portion of the container 212 within a temperature range of from 250°-350° F.

Thus, polymer (e.g. polyolefin) added to the container 212 is heated from 10–12 hours whereafter a scent or aroma imparting material which contains or consists of at least one of the cyclopentenyl-oxabicyclooctanes, cyclopentenyl-formylcyclopentenyl hydroxymethyl cyclohexenes of our invention is quickly added to the melt. The material must be compatible with the polyolefin and forms a homogeneous liquid melt therewith. The scented material containing or consisting of at least one of the cyclopentenyl-oxabicyclooctanes, cyclopentenyl-formylcyclohexenes and cyclopentenyl hydroxymethyl cyclohexenes of our invention is of a type for the particular aroma desired and formulated specifically for the scenting purpose for which the polyolefin will be employed. The heat resisting coils and aromatic materials in some instances in solid or powdered form may be employed or added to the polyolefin in the container 212. Generally about 10–30% by weight of the scenting material is added to the polyolefin.

After the scent imparting material containing or consisting of at least one of the cyclopentenyl-oxabicyclooctanes, cyclopentenyl-formylcyclohexenes and cyclopentenyl hydroxymethyl cyclohexenes of our invention is added to the container 212, the mixture is stirred for a few minutes, for example, 5-15 minutes and maintained within the temperature ranges indicated previously by the heating coils 212-A and 218, respectively. The controls 216 and 220 are connected through cables 224 and 226 to a suitable supply of electric current for supplying the power for heating purposes. The controls 216 and 220 are connected to the heating coils 212-A, respectively, through wires 214 and 222.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma imparting mixture (containing or consisting of at least one of the cyclopentenyl-oxabicyclooctanes, cyclopentenyl-formylcyclohexenes and cyclopentenyl-hydroxymethyl cyclohexenes of our invention) will continuously drop through the orifices 234 downwardly from the conduit 232. During this time, the temperature of the polymer (e.g., polyolefin) an aroma mixture containing or consisting of at least one of the cyclopentenyl-oxabicyclooctanes, cyclopentenyl-formylcyclohexenes and cyclopentenyl-hydroxymethyl cyclohexenes of our invention in the container 212 is accurately controlled so that a temperature in the range of from about 210°-275° F. will exist in the conduit 232. The regulation of the temperature through the control 216 and the control 220 is essential in order to insure temperature balance to provide for the continuous dropping or dripping of molten polymer (e.g. polyolefin) and scenting material containing or consisting of at least one of the cyclopentenyl-oxabicyclooctanes, cyclopentenyl-formylcylcohexenes and cyclopentenyl-hydroxymethyl cyclohexenes of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water or some other suitable cooling liquid in order to insure the rapid cooling of each of the pellets. The pellets 244 are then collected from the container 245 and utilized in a process as illustrated infra.

A feature of this aspect of the process of our invention is in the provision for moistening the conveyor belt 238 to insure rapid formation of the solid polymer (e.g., polyolefin) scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 250 which is continuously fed with water 254 to maintain a level for moistening a sponge element 256 which bears against the exterior surface of the belt 238.

THE INVENTION

The instant invention provides cyclopentenyl-oxabicyclooctanes, cyclopentenyl-formylcyclohexenes and cyclopentenyl-hydroxymethyl cyclohexenes defined according to the generic structures:

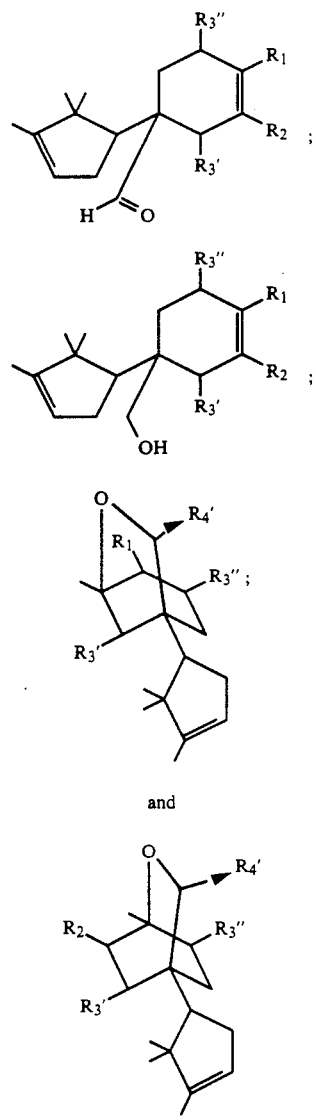

wherein $R_1$, $R_2$, $R_3'$, and $R_3''$ each represents hydrogen or methyl with the provisos:
 (i) one or two of $R_1$, $R_2$, $R_3'$ and $R_3''$ is methyl;
 (ii) $R_1$ and/or $R_2$ is methyl;
 (iii) at least one of $R_3'$ and $R_3''$ represents hydrogen; and
 (iv) when $R_1$ and $R_2$ are both methyl then each of $R_3'$ and $R_3''$ each represents hydrogen wherein $R_4'$ is hydrogen or $C_1$-$C_5$ alkyl. The cyclopentenyl-oxabicyclooctanes, cyclopentenyl-formylcyclohexenes and cyclopentenyl-hydroxymethyl cyclohexenes of our invention are useful in augmenting or enhancing the aroma of perfume compositions, colognes and perfumed articles, (including but not limited to solid or liquid anionic, cationic, nonionic or zwitterionic detergents, perfume polymers, fabric softener compositions and fabric softener articles, cosmetic powders, hair preparations and the like).

Briefly, our invention also employs the cyclopentenyl-oxabicyclooctanes, cyclopentenyl-formylcyclohexenes and cyclopentenyl-hydroxymethyl cyclohexenes of our invention to impart, augment and/or enhance cassis, camphoraceous, sweaty, borneol, woody, piney, green, and ozoney aromas with parsley, basil, cassis, sweaty, borneol, camphoraceous, eucalyptus bud-like, hemlock and piney topnotes in or to perfume compositions, colognes and perfumed articles (e.g. solid or liquid anionic, cationic, nonionic or zwitterionic detergents, perfumed polymers, fabric softener compositions, fabric softener articles, hair preparations, cosmetic powders and the like.

Briefly, the cyclopentenyl-oxabicyclooctanes, cyclopentenyl-formylcyclohexenes and cyclopentenyl-hydroxymethyl cyclohexenes of our invention may be prepared by first forming the compound having the structure:

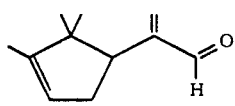

utilizing the reaction:

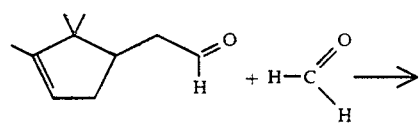

or using the reaction as set forth in U.S. Letters Pat. No. 4,610,813 at reaction scheme "3" or "5" at columns 5 and 6 or at Example 4(f) at column 13, lines 32-53 and exemplified in Example I, infra.

The resulting compound having the structure:

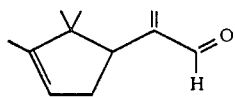

is then reacted with a diene defined according to the generic structure:

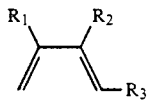

wherein $R_1$, $R_2$ and $R_3$ are the same or different methyl or hydrogen with the provisos:

(i) one or two of $R_1$, $R_2$ and $R_3'$ is methyl;
  (ii) $R_1$ and/or $R_2$ is methyl; and
  (iii) when $R_1$ and $R_2$ are both methyl then $R_3$ is hydrogen.

The Diels-Alder reaction is shown, generically, according to the following reaction:

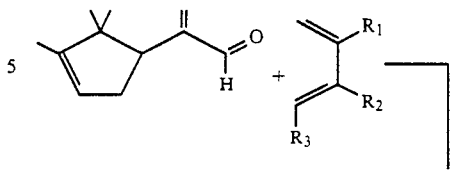

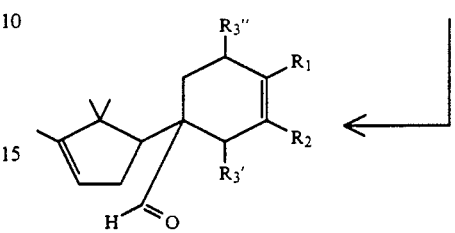

The resulting carboxaldehydes defined according to the generic structure:

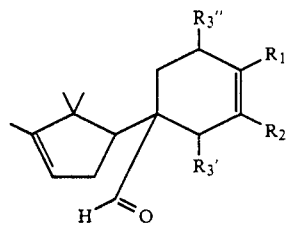

may be used "as is" for their organoleptic properties and thus they may be purified as by fractional distillation, or they may be further reacted by reduction to form the compounds defined according to the generic structure:

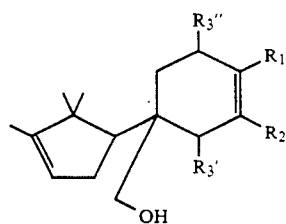

or they may be reacted via electrophilic addition to form the compounds defined according to the generic structure:

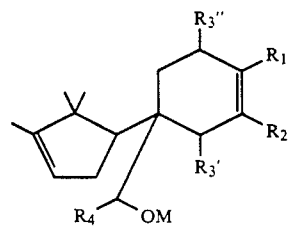

which compounds are further hydrolyzed to form the compounds defined according to the generic structure:

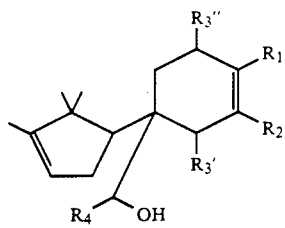

(wherein M represents MgX or Li and wherein X represents chloro, bromo or iodo). The reduction reaction is as follows:

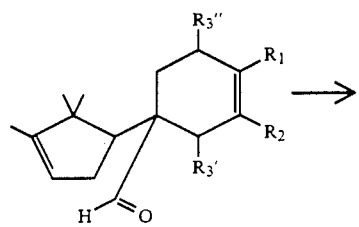

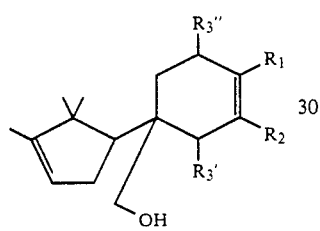

The electrophilic addition reactions are as follows:

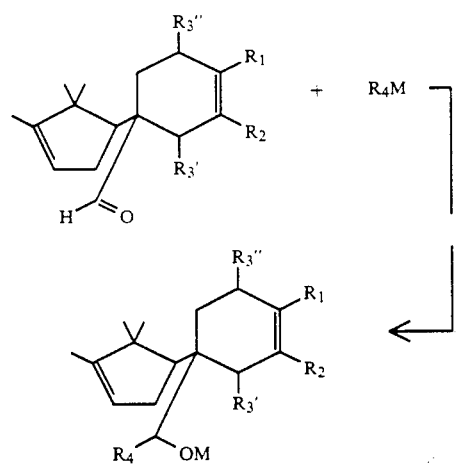

and

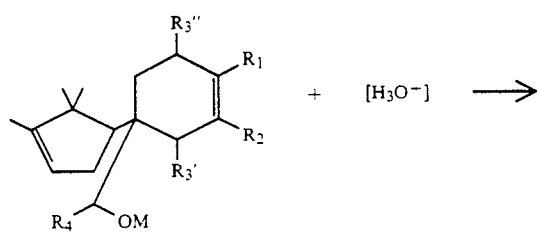

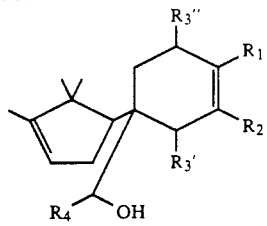

The resulting hydroxyl derivatives defined according to the generic structure:

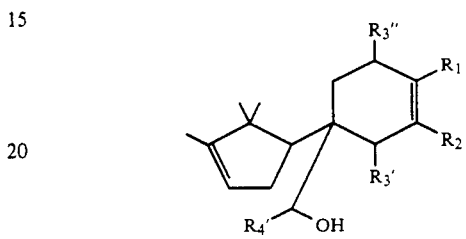

wherein $R_4'$ represents hydrogen or $C_1$-$C_5$ alkyl may be used "as is" for their organoleptic properties (and thus fractionally distilled) or they may be further reacted by means of cyclization according to the reaction:

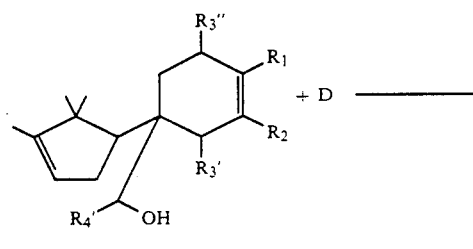

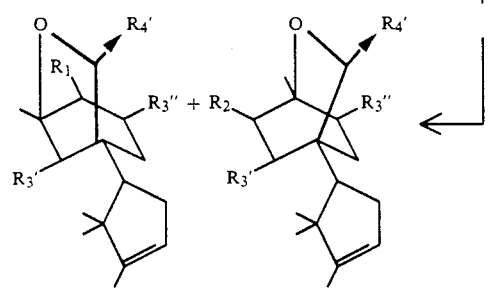

whereby the compounds having the structures:

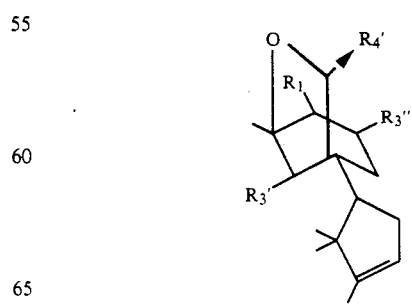

and

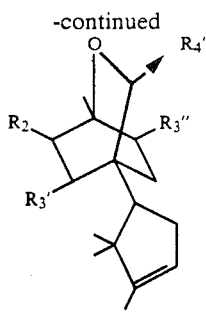

are formed in admixture.

The above reaction sequences; that is, the Diels-Alder reaction; the alcohol formation reactions (either reduction or electrophilic addition) and the cyclization reactions are carried out using the conditions substantially the same as those set forth in U.S. Letters Pat. Nos. 4,269,862 and 4,267,067, the specifications for which are incorporated by reference herein. The conditions set forth in the above stated U.S. Letters Pat. Nos. 4,269,862 and 4,267,067 are for the reaction schemes:

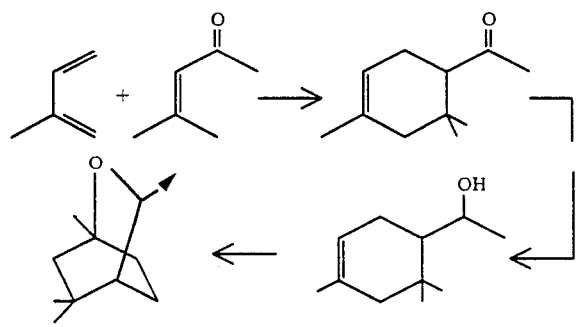

and

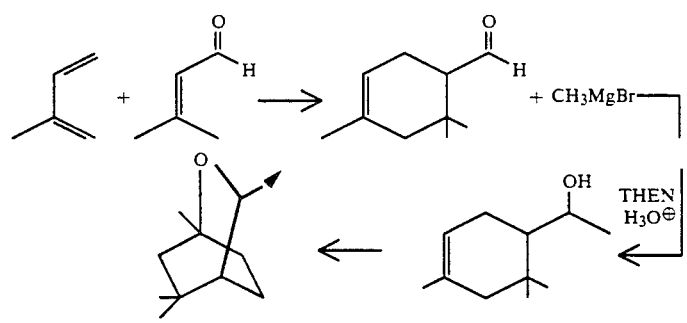

said conditions are set forth at column 5, lines 50–68, column 6, lines 1–62, column 7, lines 1–68 and column 8, lines 1–34 of U.S. Letters Pat. No. 4,269,862 as well as column 5, lines 41–68, column 6, column 7 and column 8, lines 1–29 of U.S. Letters Pat. No. 4,267,067.

Thus, the Diels-Alder reaction of the alpha, beta-unsaturated aldehyde defined according to the structure:

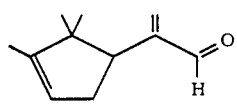

the conjugated diene having the generic structure:

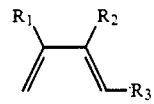

is, in general, a procedure known in the prior art. The reaction may be carried out in the presence of Lewis acid catalysts such as zinc chloride, aluminum chloride or aluminum bromide; or it may be carried out in the absence of catalysts at higher temperatures, e.g., up to 200° C. When carrying out the Diels-Alder reaction in the presence of catalysts lower temperatures, e.g. −10° C. up to 30° C. may be utilized. The Diels-Alder reaction may be carried out in the presence of or in the absence of a solvent. When solvents are used, it is preferred to use such solvents as xylene or tetralin.

That part of the reaction sequence whereby the cyclohexene carboxaldehyde (the compounds defined according the genus:

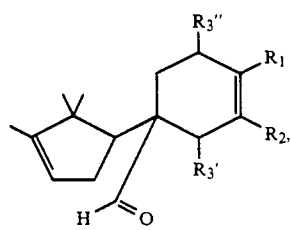

is reacted with the compound R-M (e.g., a Grignard reagent such as a $C_1$–$C_5$ alkyl magnesium halide or a $C_1$–$C_5$ alkyl lithium) to form the cyclohexene carbinol organo, metallic salt defined according the to the generic structure:

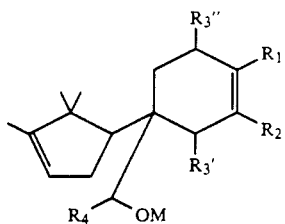

followed by hydrolysis of the cyclohexene carbinol organometallic salt to form the cyclohexene carbinol having the generic structure:

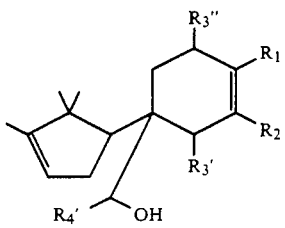

followed by cyclization of the resulting cyclohexene carbinol to form oxabicyclooctanes defined according to the generic structures:

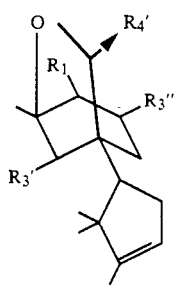

and

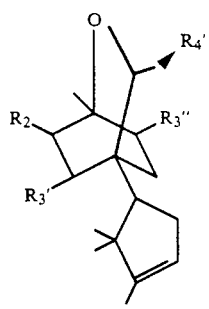

may be carried out either in one step or two steps.

In carrying out the "two-step reaction" whereby the cyclohexene carbinol is first isolated and then cyclized in the first step, that is, in the reaction of the compound R-M (e.g. a Grignard reagent) with the cyclohexene carboxaldehyde, the reaction of the compound R-M with the cyclohexene carboxaldehyde takes place in an ether solvent such as diethyl ether, tetrahydrofuran or di-n-butyl ether or another inert solvent such as toluene, chloroform or benzene to which two equivalents of ether has been added. The temperature of reaction preferably is between 0° and 100° C. with the most preferred temperature range for this reaction being from 35° C. up to 45° C.

In the two-step reaction, the resulting cyclohexene carbinol is then isolated as by distillation. The resulting cyclohexene carbinol is actually formed by means of hydrolysis of the organometallic salt defined according to the structure:

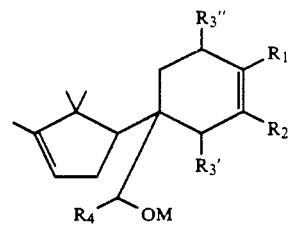

wherein M is MgX or Li and X is chloro, bromo or iodo. In the two step reaction, the resulting cyclohexene carbinol evolved from the hydrolysis reaction is then isolated as by fractional distillation. The resulting cyclohexene carbinol is then cyclized at a temperature in the range of from 25° C. up to 150° C. in the presence of an acid such as methane sulfonic acid, aqueous hydrochloric acid or sulfuric acid or phosphoric acid. The acid may be used in combination with a polar solvent such as nitromethane, toluene, methylene dichloride, 1,2-dichlorolethane, 1-nitropropane or 2-nitropropane. The cyclization in the alternative may be carried out using a Lewis Acid such as borontrifluoride, aluminum trichloride, zinc chloride, stannic chloride or zinc bromide in the presence of a solvent such as toluene, chloroform or xylene.

As stated above, the reaction of the cyclohexene carboxaldhyde to form the cyclohexene carbinol followed by cyclization may take place in a single reactor without separation of the cyclohexene carbinol. The conditions are the same as stated above for the two-step reaction.

When carrying out that part of the reaction sequence whereby the cyclohexene carboxaldehyde defined according to the generic structure:

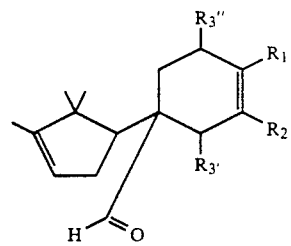

is reduced to form the compounds defined according to the generic structure:

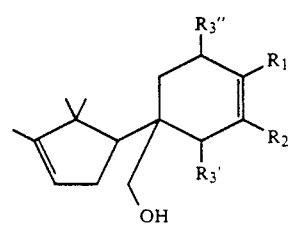

according to the reaction:

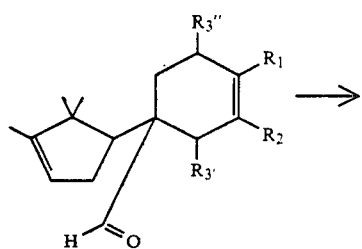

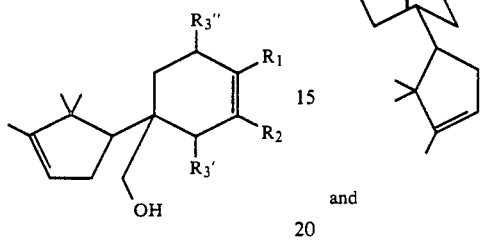

the reaction takes place in the presence of a solvent such as isopropanol, tetrahydrofuran, dioxane, diethyl ether, or diglyme using the reducing agent such as sodium borohydride, lithium aluminum hydride or VITRI-DE ® (registered trademark for the compound having the structure:

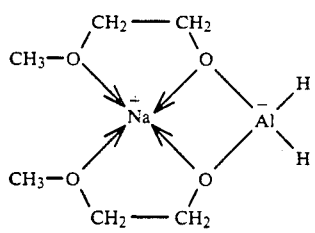

of the Hexcel Company).

In the reaction:

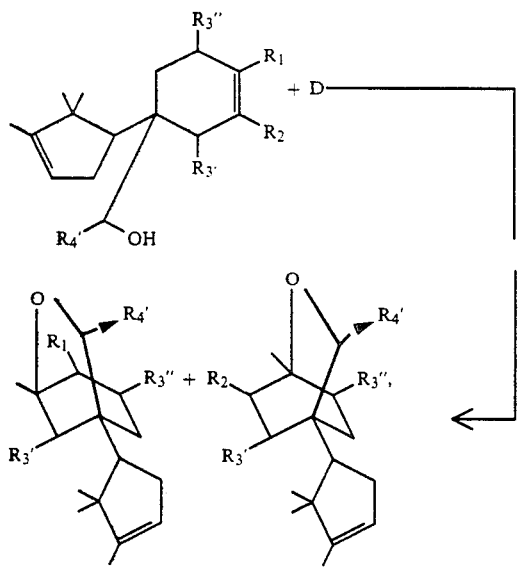

"D" stands for "cyclization reagent" such as methane sulfonic acid or sulfuric acid.

The following table sets forth specific products produced according to our invention and their perfumery properties:

TABLE I

| Product Identification | Perfumery Property |
| --- | --- |
| Mixture of compounds having the structures:<br><br>[structure]<br><br>and<br><br>[structure]<br><br>prepared according to Example V, bulked distillation fractions 9-17. | A cassis, camphoraceous, sweaty, borneol aroma with parsley, basil, cassis, sweaty, borneol-like, camphoraceous and eucalyptus bud-like topnotes. |
| Mixture of compounds having the structures:<br><br>[structure]<br><br>and<br><br>[structure]<br><br>prepared according to Example IV, bulked distillation fractions 6-8. | A cassis, woody and piney aroma with hemlock, piney, and cassis topnotes. |
| Mixture of compounds having the structures: | A green, ozoney and piney aroma profile. |

TABLE I-continued

| Product Identification | Perfumery Property |
|---|---|
| (structure) and (structure) prepared according to Example II, bulked distillation fractions 8-9. | |

At least one of the cyclopentenyl-oxabicyclooctanes, cyclopentenyl-formylcylcohexenes and cyclopentenyl-hydroxymethyl cyclohexenes of our invention and one or more auxiliary perfume ingredients including, for example, alcohols (other than the alcohols of our invention), aldehydes (other than the aldehydes of our invention), ketones, terpenic hydrocarbons, esters, lactones, ethers (other than the ethers of our invention), natural essential oils and synthetic essential oils may be admixed so that the combined odors of the individual components produce a pleasant and desired fragrance, particularly and preferably in the cassis and pine fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, at least one of the cyclopentenyl-oxabicyclooctanes, cyclopentenyl-formylcyclohexenes and cyclopentenyl-hydroxymethyl cyclohexenes of our invention can be used to alter, modify or enhance the aroma characteristics of a perfume composition, for example, by utilizing or moderating the olfactory reaction contributed by another ingredient in the composition.

The amount of one or more of the cyclopentenyl-oxabicyclooctanes, cyclopentenyl-formylcyclohexenes and hydroxymethyl cyclohexenes of our invention which will be effective in the perfume compositions as well as in the perfumed articles and colognes depends on many factors including the other ingredients, their amounts and the effects which are desired. It is been found that perfume compositions containing as little as 0.01% of at least one of the cyclopentenyl-oxabicyclooctanes, cyclopentenyl-formylcyclohexenes and cyclopentenyl-hydroxymethyl cyclohexenes of our invention or even less (e.g. 0.005%) can be used to impart, augment or enhance cassis, camphoraceous, sweaty, borneol, woody, piney, green and ozoney aroma nuances with parsley, basil, cassis, sweaty, borneol, camphoraceous, eucalpytus bud-like, hemlock and piney topnotes to soaps, cosmetics, solid or liquid anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the cyclopentenyl-oxabicyclooctanes, cyclopentenyl-formylcyclohexenes and cyclopentenyl-hydroxymethyl cyclohexenes of our invention are useful (taken alone or together with other ingredients in perfume compositions) as (an) olfactory component(s) in detergents and soaps, space ordorants and deodorants, perfumes, colognes, toilet water, bath preparations such as creams deodorants, hand lotions and sun screens; powders such as talcs, dusting powders, face powders and the like. When used as (an) olfactory component(s) as little as 1% of at least one of the cyclopentenyl-oxabicyclooctanes, cyclopentenyl-formylcyclohexenes and cyclopentenyl-hydroxymethyl cyclohexenes of our invention or even less will suffice to impart intense and substantive cassis, camphoraceous, sweaty, borneol, woody, piney, green and ozoney aroma nuances with parsley, basil, cassis, sweaty, borneol, camphoraceous, eucalpytus bud-like, hemlock and piney topnotes to pine formulations and to cassis formulations. Generally, no more than 20% of at least one of the cyclopentenyl-oxabicyclooctanes, cyclopentenyl-formylcyclohexenes and cyclopentenyl-hydroxymethyl cyclohexenes of our invention based on the ultimate end product required in the perfume composition.

Accordingly, in perfume compositions and colognes from about 0.01% up to about 70% of the perfume composition may be at least one of the cyclopentenyl-oxabicyclooctanes, cyclopentenyl-formylcyclohexenes and cyclopentenyl-hydroxymethyl cyclohexenes of our invention. In perfumed articles, the quantity of at least one of the cyclopentenyl-oxabicyclooctanes, cyclopentenyl-formylcyclohexenes and cyclopentenyl-hydroxymethyl cyclohexenes of our invention in a perfumed article may vary from about 0.005% up to about 25% of the perfumed article. In the case of perfumed polymers, for example, and up to about 8% in the case of solid or liquid anionic, cationic, nonionic or zwitterionic detergents, for example.

In addition, the perfume composition or fragrance composition of our invention can contain a vehicle or carrier for at least one of the cyclopentenyl-oxabicyclooctanes, cyclopentenyl-formylcyclohexenes and cyclopentenyl-hydroxymethyl cyclohexenes of our invention. The vehicle can be a liquid such as a non-toxic alcohol such as ethyl alcohol or a non-toxic gylcol such as propylene gylcol or the like. The carrier can also be an absorbent solid, such as a gum (e.g., gum arabic, xanthan gum, or guar gum or mixtures of same) or components for encapsulating the composition (such as gelatin as by means of coacervation or such as ureaformaldehyde prepolymer when a polymeric wall is intended to be formed around a liquid perfume composition center).

The following Examples I-V serve to illustrate the processes for preparing the compounds of our invention and compounds useful for their organoleptic properties. Examples following Example V (Examples VI et seq.) illustrate organoleptic utilities of the cyclopentenyl-oxabicyclooctanes, cyclopentenyl-formylcyclohexenes and cyclopentenyl-hydroxymethyl cyclohexenes of our invention.

All parts and percentages given here are by weight unless otherwise specified.

EXAMPLE I

Preparation of Alpha-Methylene Campholenic Aldehyde

Reaction:

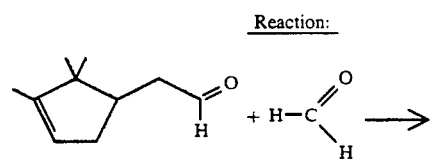

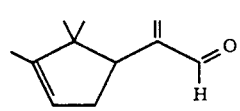

Into a twelve liter Morton flask equipped with stirrer, thermometer, reflux condenser, heating mantle, and addition funnel are placed 89 grams (0.69 moles) of di-n-butyl amine and 42 grams (0.69 moles) of acetic acid. The resulting reaction mass temperature rises to 50° C. (as a result of salt formation to form di-n-butyl amine acetate). The reaction mass is cooled to 38° C. and rapidly, 1600 grams (19.74 moles) of 37% formaldehyde (effective weight 592 grams) is added to the reaction mass.

The reaction mass is heated to 70° C. While maintaining the reaction temperature at between 70° and 72° C., over a period of 5 hours, 2000 grams (13.2 moles) of campholenic aldehyde is added to the reaction mass. The reaction mass is then stirred for an additional period of 8 hours while maintaining the reaction mass at 70° C.

The reaction mass now exists in two phases; an organic phase and an aqueous phase. The organic phase is washed with 2 liters of water followed by saturated sodium chloride; followed by 500 ml 10% sodium bicarbonate followed by 1000 ml saturated sodium chloride.

The organic phase is filtered through anhydrous magnesium sulfate and rushed over to yield 1601 grams of product.

The resulting product is then fractionally distilled yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 48/80 | 78/89 | 3.72/4.22 | 655 |
| 2 | 78 | 97 | 3.56 | 691 |
| 3 | 94 | 160 | 3.20 | 391 |
| 4 | 110 | 163 | 2.42 | 15 |

FIG. 1 is the GLC profile of the reaction product. The peak indicated by reference numeral 10 is the peak for the compound having the structure:

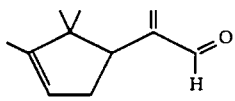

(Conditions: Carbowax column, programmed to 220° C. isothermal).

EXAMPLE II

Preparation of Formyl Cyclopentenyl Cyclohexene

Reaction:

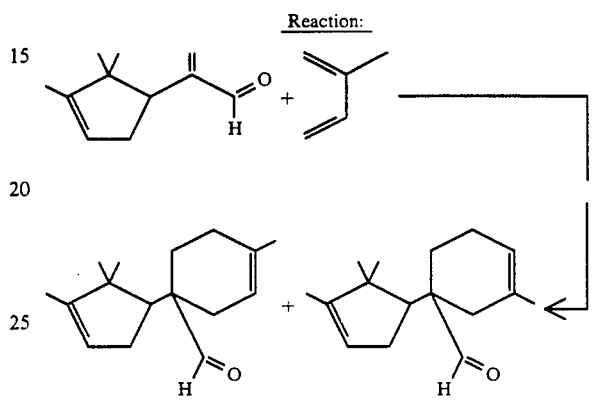

Into a two liter Parr Bomb is charged 590 grams (3.73 moles) of the compound having the structure:

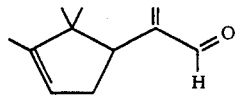

prepared according to Example I and 305 grams (4.48 moles) of isoprene having the structure:

The Parr Bomb is closed and the temperature is raised to 140° C. and the pressure is raised to 180 psig. The Parr Bomb is maintained at 140° C. at 180 psig for a period of 0.5 hours. The bomb is then heated to 170° C. while maintaining the pressure at 180 psig and maintained at that temperature and pressure for 12 hours. The Parr Bomb is then cooled and opened and the resulting product is fractionally distilled on an 18 inch × 1.5 inch Goodloe distillation column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 60/140 | 145/150 | 0.895/0.72 | 9/1 |
| 2 | 128 | 145 | 0.69 | 9/1 |
| 3 | 128 | 146 | 0.685 | 9/1 |
| 4 | 127 | 148 | 0.740 | 9/1 |
| 5 | 128 | 148 | 1.0 | 9/1 |
| 6 | 128 | 145 | 0.978 | 2/1 |
| 7 | 148 | 152 | 0.918 | |
| 8 | 141 | 149 | 0.918 | 2/1 |
| 9 | 122 | 147 | 0.984 | 2/1 |
| 10 | 113 | 145 | 0.972 | 2/1 |
| 11 | 112 | 147 | 0.954 | 2/1 |

-continued

| Fraction No. | Vapor Temp. (°C.) | Liquid Temp. (°C.) | Vacuum mm/Hg. Pressure | Reflux Ratio |
|---|---|---|---|---|
| 12 | 110 | 155 | 0.954 | 2/1 |
| 13 | 109 | 178 | 0.960 | 2/1 |
| 14 | 95 | 200 | 0.960 | 2/1 |
| 15 | 95 | 210 | 0.918 | 2/1 |

Fractions 8, 9 and 10 are bulked. The bulked fractions 8, 9 and 10 have a green, ozoney and piney aroma profile. The resulting product is a mixture of compounds having the structures:

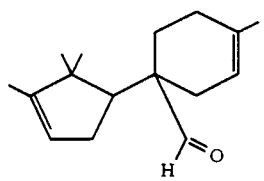

and

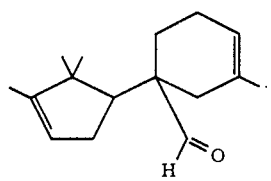

FIG. 2 is the GLC profile for the reaction product. The peaks indicated by reference numeral 20 are the peaks for the compounds having the structures:

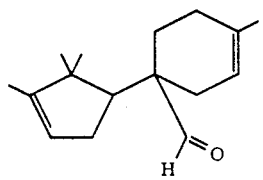

and

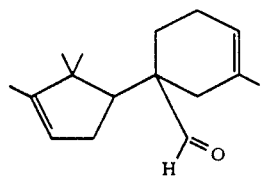

(and isomers thereof. (Conditions: Carbowax column, programmed at 220° C. isothermal).

FIG. 3 is the NMR spectrum for the mixture of compounds having the structures:

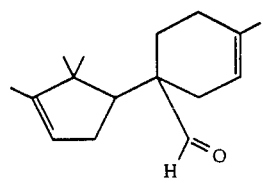

and

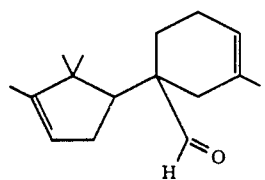

EXAMPLE III

Preparation of Cyclopentenyl Hydroxymethyl Cyclohexene Derivative

Reaction:

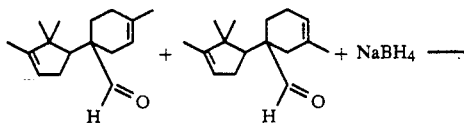

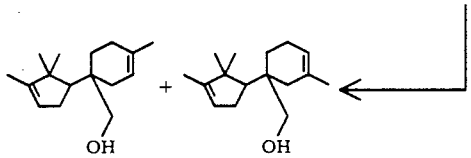

Into an one liter reaction flask equipped with stirrer, thermometer, reflux condenser, heating mantle and addition funnel is placed 19 grams (0.50 moles) of sodium borohydride and a mixture of 200 ml isopropyl alcohol and 150 ml water. The resulting mixture with stirring is maintained at 24° C. While maintaining the resulting mixture at 24° C., the mixture of compounds having the structures:

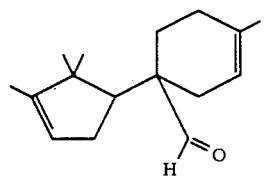

and

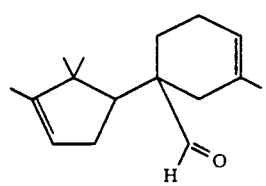

according to Example II is added to the reaction mass (230 grams, 0.99 moles) over a period 2 hours. The temperature is allowed to rise to 47° C.

The reaction mass is then aged for a period of 6.5 hours while it cools to room temperature on its own.

The reaction mass now exists in two phases; an organic phase and an aqueous phase. The aqueous phase is drawn off and the organic phase is washed with 400 ml saturated sodium chloride and then filtered through anhydrous magnesium sulfate. The reaction mass is then concentrated to yield 225 grams of crude product (0.96 moles, 97%).

FIG. 4 is the GLC profile for the reaction product containing the compounds having the structures:

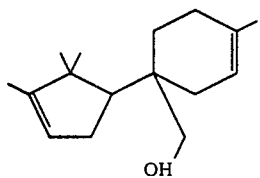

and

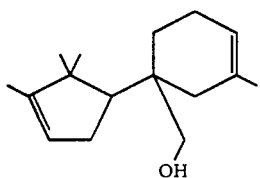

(Conditions: Carbowax column, programmed at 150°-220° C.). The peaks indicated by reference numerals 40, 42 and 44 are the peaks for the isomers of the compounds having the structures:

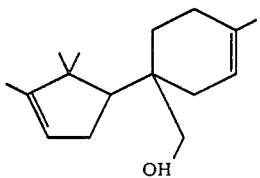

and

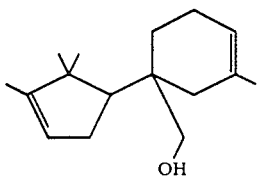

FIG. 5 is the infra-red spectrum for the mixture of compounds having the structures:

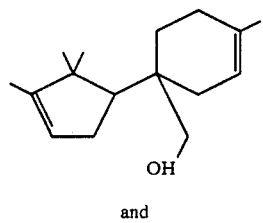

and

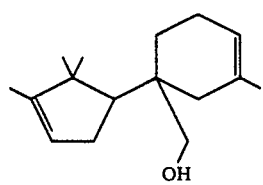

FIG. 6 is the NMR spectrum for the mixture of compounds having the structures:

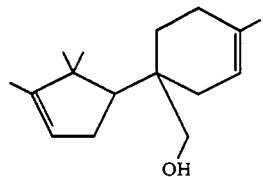

and

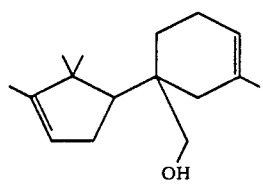

The sections of the spectrum marked in detail as "6-A", "6-B" and "6-C" are shown in detail in FIGS. 6-A, 6-B and 6-C.

EXAMPLE IV

Preparation of Oxabicyclooctane Derivative

Reaction:

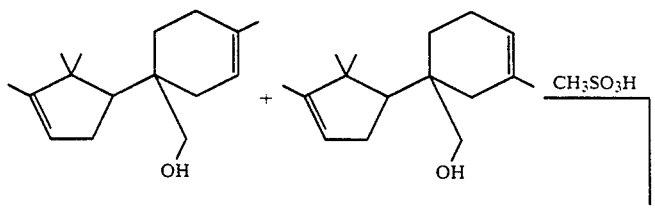

Reaction:

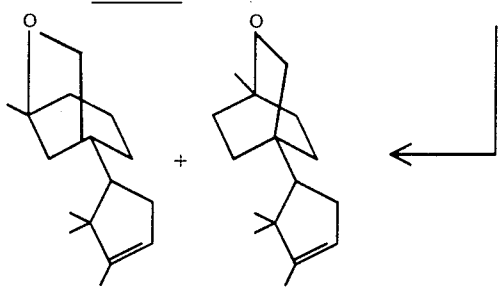

Into an one liter reaction flask equipped with stirrer, thermometer, reflux condenser, heating mantle and addition funnel is placed 255 grams (0.96 moles) of the mixture of the compounds having the structures:

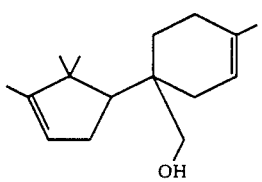

and

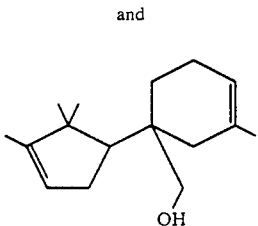

prepared according Example III and 300 ml of nitromethane. The reaction mass is maintained at 25°-26° C. Slowly over a period of 5 minutes, 2.76 grams (0.028 moles) of methane sulfonic acid is added to the reaction mass.

The reaction mass, with stirring is then heated to 60° C. and maintained at 60° C. for a period of 5 hours. At the end of the 5 hour period 200 ml of 10% sodium bicarbonate is added to the reaction mass. The reaction mass is then stirred for an additional 30 minutes. The reaction mass is then aged for 72 hours. At the end of the 72 hour period, 250 ml water followed by 50 ml toluene is added to the reaction mass. The organic phase is separated from the aqueous phase and the organic phase is washed with 250 ml of saturated sodium chloride. The reaction mass is then filtered through anhydrous magnesium sulfate and rushed over to yield 165 grams (0.71 moles) of product (73% yield). The reaction mass is then fractionally distilled yielding the following fractions:

| Fraction No. | Vapor Temp. (°C.) | Liquid Temp. (°C.) | Vacuum mm/Hg. Pressure |
|---|---|---|---|
| 1 | 32/45 | 45/93 | 105/267 |
| 2 | 110 | 738 | 2.87 |
| 3 | 126 | 740 | 2.52 |
| 4 | 130 | 140 | 2.67 |
| 5 | 130 | 142 | 2.56 |
| 6 | 132 | 143 | 2.63 |
| 7 | 134 | 144 | 2.76 |
| 8 | 134 | 146 | 2.76 |

| Fraction No. | Vapor Temp. (°C.) | Liquid Temp. (°C.) | Vacuum mm/Hg. Pressure |
|---|---|---|---|
| 9 | 134 | 153 | 2.76 |
| 10 | 131 | 162 | 2.87 |
| 11 | 132 | 173 | 2.70 |
| 12 | 110 | 233 | 3.10 |

FIG. 7 is the GLC profile for the reaction product prior to distillation containing the compounds having the structures:

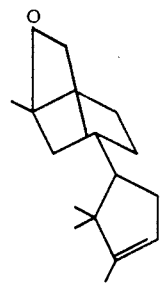

and

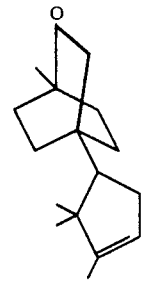

(Conditions: Carbowax column, programmed at 220° isothermal). The peaks indicated by reference numerals 70, 72 and 74 are for the compounds and their isomers having the structures:

31
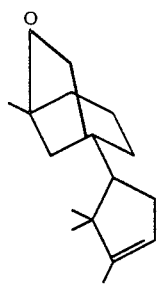
and
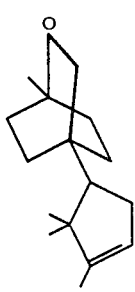
FIG. 8 is the infra-red spectrum for the mixture of compounds having the structures:
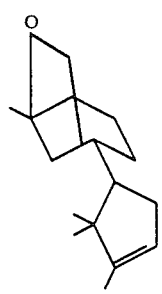
and
32
-continued
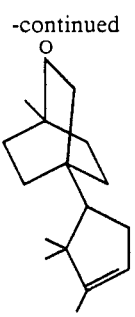
FIG. 9 is the NMR spectrum for the mixture of compounds having the structures:
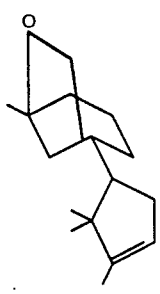
and
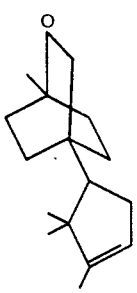
Both distillation fractions 6–8 having a cassis, woody and piney aroma with hemlock, piney and cassis topnotes.
EXAMPLE V
Preparation of Oxabicyclooctane Derivative
Reaction:
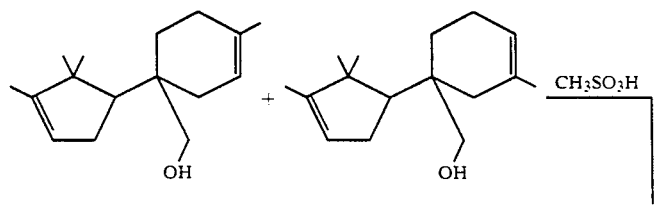

Reaction:

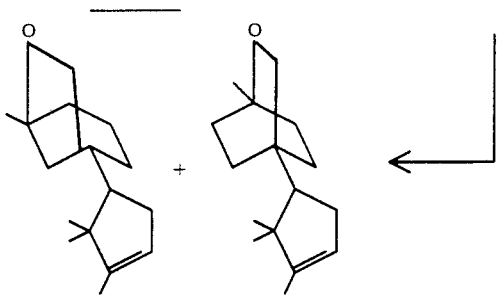

Into a three liter reaction flask equipped with stirrer, thermometer, reflux condenser and addition funnel is placed 660 grams (2.82 moles) of the mixture of compounds having the structures:

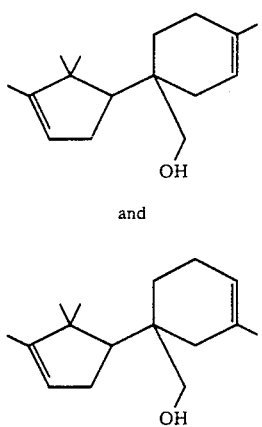

prepared according to the procedure of Example III and 600 ml of nitromethane. While maintaining the reaction temperature at 34° C., 13.50 grams (0.14 moles of methane sulfonic acid is added to the reaction mass. The reaction mass is then heated to 60° C. and maintained at 60° C. with stirring for a period of 5.5 hours. At the end of the 5.5 hour period, 600 ml, 10% sodium bicarbonate is added to the reaction mass and the reaction mass is stirred for a period of 0.5 hours at 60° C. The reaction mass then partitions into three layers upon cooling. The aqueous phase is drawn off as is the nitromethane phase. The aqueous phase is extracted with 100 ml diethyl ether. The organic phase and the diethyl ether extract are combined and washed with 500 ml saturated sodium chloride; and then dried over anhydrous magnesium sulfate and filtered and concentrated to 593 grams (2.53 moles). The resulting product is distilled yielding 477 grams of product (2.04 moles) and yielding the following fractions:

| Fraction No. | Vapor Temp. (°C.) | Liquid Temp. (°C.) | Vacuum mm/Hg. Pressure |
|---|---|---|---|
| 1 | 55/118 | 129/130 | 2.79/2.77 |
| 2 | 120 | 131 | 2.74 |
| 3 | 120 | 132 | 2.73 |
| 4 | 120 | 133 | 2.70 |
| 5 | 120 | 133 | 2.69 |
| 6 | 121 | 133 | 2.69 |
| 7 | 120 | 133 | 2.69 |
| 8 | 120 | 134 | 2.67 |
| 9 | 121 | 134 | 2.66 |

| Fraction No. | Vapor Temp. (°C.) | Liquid Temp. (°C.) | Vacuum mm/Hg. Pressure |
|---|---|---|---|
| 10 | 120 | 135 | 2.66 |
| 11 | 120 | 135 | 2.66 |
| 12 | 121 | 136 | 2.64 |
| 13 | 120 | 136 | 2.63 |
| 14 | 122 | 137 | 2.63 |
| 15 | 122 | 138 | 2.63 |
| 16 | 122 | 145 | 2.63 |
| 17 | 122 | 145 | 2.63 |
| 18 | 122 | 148 | 2.61 |
| 19 | 122 | 156 | 2.61 |
| 20 | 115 | 200 | 2.60 |

Bulked fractions 9-17 have a cassis, camphoraceous, sweaty, borneol aroma with parsley, basil, cassis, sweaty, borneol like, camphoraceous and eucalyptus bud-like topnotes.

FIG. 10 is the GLC profile of the reaction product (Conditions: Carbowax column programmed at 220° isothermal). The peaks indicated by reference numerals 102, 104, 106 and 100 are the peaks for the compounds having the structures:

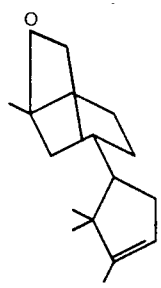

and

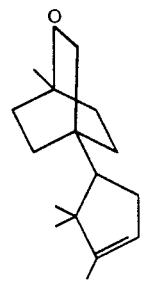

and their isomers.

EXAMPLE VI

The cyclopentenyl-oxabicyclooctanes, cyclopentenyl-formylcyclohexenes and cyclopentenyl-hydroxymethyl cyclohexenes of our invention produced according to Examples I-V inclusive have very long lasting cassis, camphoraceous, sweaty, borneol, woody, piney, green and ozoney aromas with parsley, basil, cassis, sweaty, borneol, camphoraceous, eucalyptus bud-like, hemlock and piney topnotes which may be utilized to a great extent in inexpensive functional products. The following pine fragrance demonstrates the use of these material sin perfume compositions:

| INGREDIENTS | PARTS BY WEIGHT | | |
|---|---|---|---|
| | VIA | VIB | VIC |
| Isobornyl acetate | 100 | 100 | 100 |
| Camphor | 10 | 10 | 10 |
| Terpineol | 25 | 25 | 25 |
| Fir Balsam Absolute (50% in Diethyl Phthalate) | 20 | 20 | 20 |
| Coumarin | 4 | 4 | 4 |
| Linalool | 30 | 30 | 30 |
| Anethol | 2 | 2 | 2 |
| Fenchyl Alcohol | 10 | 10 | 10 |
| Lemon Terpenes Washed | 50 | 50 | 50 |
| Borneol | 5 | 5 | 5 |
| Galbanum Oil | 5 | 5 | 5 |
| Turpentine Russian | 150 | 150 | 150 |
| Pinus Pimilionus | 50 | 50 | 50 |
| Eucalyptol | 50 | 50 | 50 |
| 2,2,6-trimethyl-1-cyclohexene-1-carboxaldehyde | 5 | 5 | 5 |
| Maltol (1% in Diethyl Phthalate) | 5 | 5 | 5 |
| Mixture of compounds having the structures: | 12 | 0 | 0 |

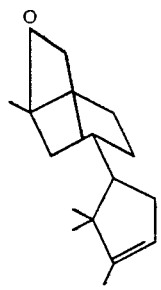

and

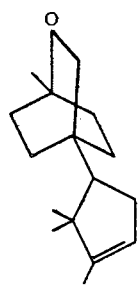

prepared according to Example IV, bulked distillation fractions 9-17.

| | | | |
|---|---|---|---|
| Mixture of compounds having the structures: | 0 | 12 | 0 |

and

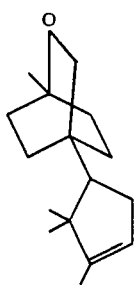

prepared according to Example IV, bulked distillation fractions 6-8.

| | | | |
|---|---|---|---|
| Mixture of compounds having the structures: | 0 | 0 | 12 |

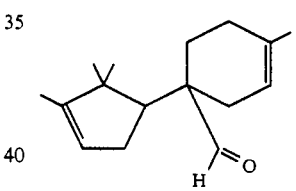

and

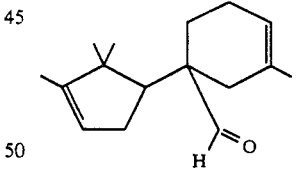

prepared according to Example II, bulked distillation fractions 8 and 9.

The mixture of compounds having the structures:

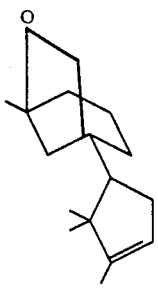

prepared according to Example V adds to this pine fragrance cassis, camphoraceous and sweaty, animalic undertones with parsley, basil, cassis, sweaty, borneol-like, camphoraceous and eucalyptus bud-like topnotes. Accordingly, the fragrance of Example VIA can be described as "piney with cassis, camphoraceous, sweaty and animalic undertones and parsley, basil, cassis, sweaty, borneol-like, camphoraceous and eucalyptus bud-like topnotes".

The mixture of compounds having the structures:

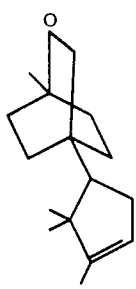

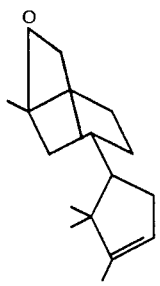

prepared according to Example IV, bulked distillation fractions 6-8 adds to this pine fragrance cassis and woody undertones and hemlock and cassis topnotes. Accordingly, the pine fragrance of Example VIB can be described as "piney with cassis and woody undertones and hemlock and cassis topnotes".

The mixture of compounds having the structures:

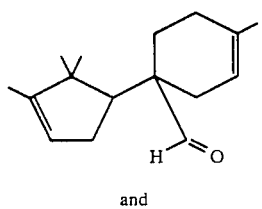

and

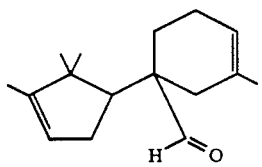

prepared according to Example II adds to this pine formulation green and ozoney undertones. Accordingly, the pine fragrance of Example VIC can be described as "piney with green and ozoney undertones".

EXAMPLE VII

A Cosmetic Powder Preparation

A cosmetic powder is prepared by mixing in a ball mill 100 grams of talcum powder with 0.25 grams of one of the substances set forth in Table II below containing at least one of the cyclopentenyl-oxabicyclooctanes, cyclopentenyl-formylcyclohexenes cyclohexenes and cyclopentenyl-hydroxymethyl cyclohexenes of our invention. Each of the cosmetic powders has an excellent aroma as described in Table II below.

TABLE II

| PERFUMERY SUBSTANCE | AROMA NUANCE |
|---|---|
| Mixture of compounds having the structures: 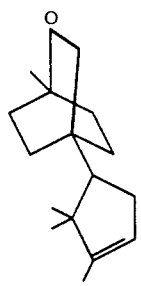 prepared according to Example V, bulked distillation fractions 9-17. | A cassis, camphoraceous sweaty and borneol aroma with parsley, basil, cassis, sweaty, borneol-like, camphoraceous and eucalyptus bud-like topnotes. |
| Mixture of compounds having the structures: | A cassis, woody and piney aroma with hemlock, piney and cassis topnotes. |

TABLE II-continued

| PERFUMERY SUBSTANCE | AROMA NUANCE |
|---|---|
| 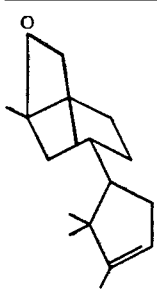 and 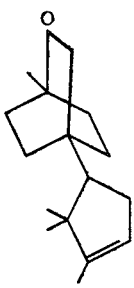 prepared according to Example IV, bulked distillation fractions 6-8. | |
| Mixture of compounds having the structures: 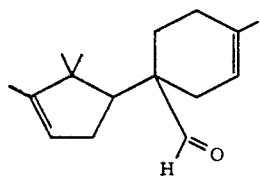 and 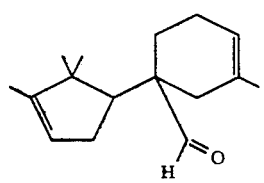 prepared according to Example II, bulked distillation fractions 8 and 9. | A green, ozoney and piney aroma profile. |
| Perfume composition of Example VIA: | Piney with cassis, camphoraceous, sweaty and animalic undertones and parsley, basil, cassis, sweaty, borneol-like, camphoraceous and eucalyptus bud-like topnotes. |
| Perfume composition of Example VIB: | Piney with cassis and woody undertones and hemlock and cassis topnotes. |
| Perfume composition of Example VIC: | Piney with green and ozoney undertones. |

EXAMPLE VIII

Perfumed Liquid Detergent

Concentrated liquid detergents (Lysine salt of n-dodecylbenzene sulfonic acid as more specifically described in U.S. Pat. No. 3,948,818 issued on Apr. 6, 1976, the specification for which is incorporated herein) with aromas as set forth in Table II of Example VII, supra are prepared containing 0.10%, 0.15, 0.20%, 0.25%, 0.30% and 0.35% of each of the substances of Table II of Example VII. They are prepared by adding and homogeneously admixing the appropriate quantity of one of the substances of Table II of Example VII in the liquid detergent. The detergents all possess excellent aromas as set forth in Table II of Example VII.

EXAMPLE IX

Preparation of a Cologne And Handkerchief Perfume

The substances set forth in Table II of Example VII are incorporated separately into colognes at concentrations of 2.0%, 2.5%, 3.0%, 3.5%, 4.0%, 4.5% and 5.0% in 75%, 80%, 85% and 90% aqueous food grade ethanol solutions; and into handkerchief perfumes at concentrations of 15%, 20%, 25% and 30%, in 80%, 85%, 90% and 95% aqueous food grade ethanol solutions. Distinctive aromas as set forth in Table II of Example VII, supra are imparted to the colognes and to the handkerchief perfume compositions at all levels indicated.

EXAMPLE X

Preparation of Soap Composition

One hundred grams of soap chips (IVORY ®, produced by the Procter & Gamble Company, of Cincinnati, Ohio) are admixed with 1 gram of each of the substances of Table II of Example VII, supra until homogeneous compositions are obtained. The homogeneous compositions are each separated then heated under 3 atmospheres pressure at 180° C. for a period of 3 hours and the resulting liquid samples are place in soap molds. The resulting soap cake, on cooling, manifest excellent long-lasting aromas as set forth in Table II of Example VII, supra.

EXAMPLE XI

Preparation of Solid Detergent Compositions

Detergents are prepared from the following ingredients according to Example II of Canadian Letters Patent No. 1,007,948 the specification for which is incorporated by reference herein:

| INGREDIENTS | PARTS BY WEIGHT |
|---|---|
| Neodol ® 45-11 (a C$_{14}$-C$_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table II of Example VII. Each of the detergent samples has an excellent aromas as set forth in Table II of Example VII.

EXAMPLE XII

Dryer-Added Fabric Softener Article

Utilizing the procedure of Example II at column 15 of U.S. Pat. No. 3,623,396, the specification for which is incorporated by reference herein, a non-woven cloth substrate useful as a dryer-added fabric softening article of manufacture is prepared wherein the substrate, the substrate coating and the outer coating and the perfuming material are as follows:

1. A water "dissolvable" paper ("Dissolvo Paper")
2. Adogen 448 (m.p. about 140° F.) as the substrate coating; and
3. An outer coating have the following formulation (m.p. about 150° F.):
   57% $C_{20-22}$ HAPS
   22% isopropyl alcohol
   20% antistatic agent
   1% of one of the substances of Table II of Example VII, supra Fabric softening compositions containing one of the substances of Table II of Examples VII consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and outer coating weight ratio of about 1:1 by weight of the substrate.

Pleasant aromas as set forth in Table II of Example VII are imparted to the head space in the dryer on operation thereof using the said drier-added fabric softening non-woven fabric.

What is claimed is:

1. A cyclopentenyl-oxabicyclooctane, cyclopentenyl-formylcyclohexene and/or cyclopentenyl-hydroxymethyl cyclohexene having a structure selected from the group consisting of:

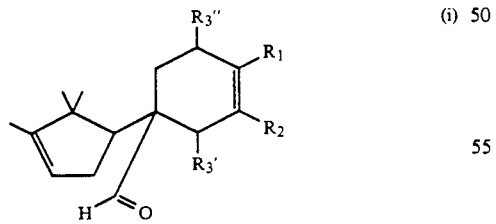
(i)

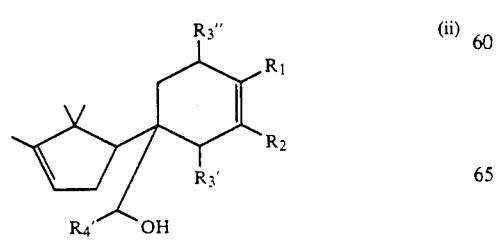
(ii)

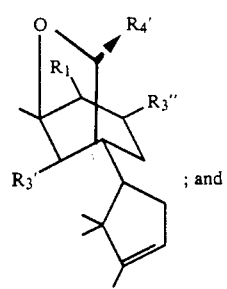
(iii) ; and

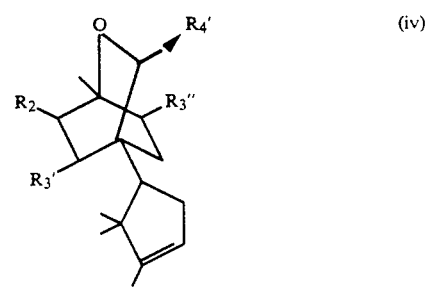
(iv)

wherein $R_1$, $R_2$, $R_3'$, and $R_3''$ each represents hydrogen or methyl with the provisos:

(i) one or two of $R_1$, $R_2$, $R_3'$, and $R_3''$ is methyl;
(ii) $R_1$ and/or $R_2$ represents methyl;
(iii) at least one of $R_3'$ and $R_3''$ is hydrogen; and
(iv) when $R_1$ and $R_2$ is methyl then $R_3'$ and $R_3''$ represents hydrogen and wherein $R_4'$ is hydrogen or $C_1$–$C_5$ alkyl.

2. A compound of claim 1 defined according to the structure:

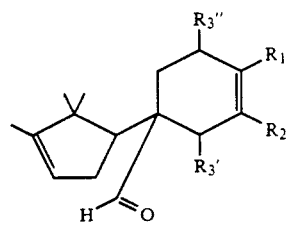

3. A compound of claim 1 defined according to the structure:

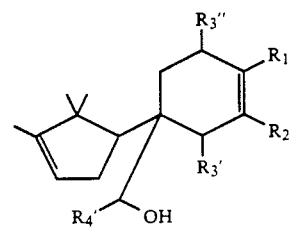

4. A compound of claim 1 defined according to the structure:

5. A compound of claim 1 defined according to the structure:
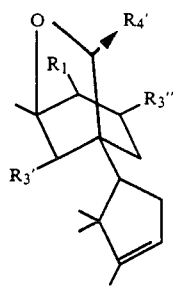
6. A mixture of compounds defined according to claim 1 having the structures:
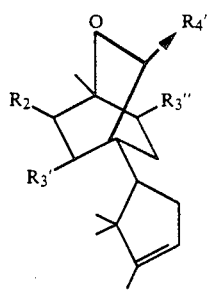
and
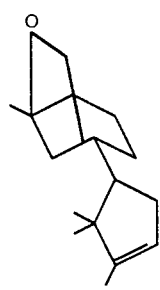
-continued
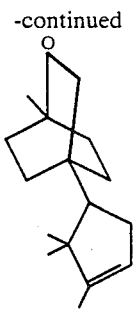
7. A mixture of compounds of claim 1 having the structures:
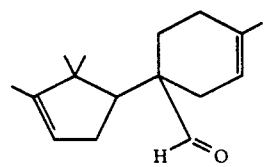
and
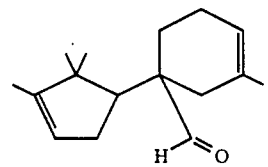
8. A mixture of compounds of claim 1 having the structures:
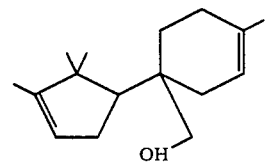
and
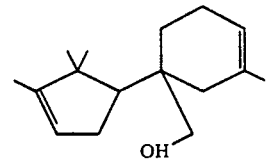
* * * * *